US011109490B1

(12) United States Patent
Speck et al.

(10) Patent No.: US 11,109,490 B1
(45) Date of Patent: Aug. 31, 2021

(54) MANUFACTURING IMPLANTABLE TISSUE STIMULATORS

(71) Applicant: Micron Medical LLC, Boca Raton, FL (US)

(72) Inventors: Benjamin Speck, Boca Raton, FL (US); Graham Patrick Greene, Boca Raton, FL (US)

(73) Assignee: Micron Medical LLC, Boca Raton, FL (US)

( * ) Notice: Subject to any disclaimer, the term of this patent is extended or adjusted under 35 U.S.C. 154(b) by 0 days.

(21) Appl. No.: 16/825,003

(22) Filed: Mar. 20, 2020

(51) Int. Cl.
*H05K 3/28* (2006.01)
*A61N 1/05* (2006.01)
*H05K 3/40* (2006.01)
*B29C 45/14* (2006.01)
*B29C 45/16* (2006.01)
*B29C 41/14* (2006.01)
*B29K 75/00* (2006.01)
*B29L 31/34* (2006.01)

(52) U.S. Cl.
CPC .......... *H05K 3/284* (2013.01); *A61N 1/0551* (2013.01); *B29C 41/14* (2013.01); *B29C 45/14639* (2013.01); *B29C 45/1671* (2013.01); *H05K 3/4007* (2013.01); *B29K 2075/00* (2013.01); *B29L 2031/3425* (2013.01); *H05K 2203/1316* (2013.01); *H05K 2203/1327* (2013.01); *H05K 2203/1361* (2013.01)

(58) Field of Classification Search
CPC ............... H05K 3/284; H05K 3/4007; H05K 2203/1316; H05K 2203/1327; H05K 2203/1361; B29C 45/1671; B29C 45/14639; B29C 41/14; A61N 1/0551; B29K 2075/00; B29L 2031/3425
See application file for complete search history.

(56) References Cited

U.S. PATENT DOCUMENTS 4,959,706 A * 9/1990 Cusack ................... H01L 24/05
257/786
7,894,915 B1 * 2/2011 Chitre ..................... A61N 1/05
607/123

OTHER PUBLICATIONS

LeGere, "Overmolding Electronics: The Benefits of The Low-Pressure Molding Process", Jul. 2, 2018, https://www.iconnsystems.com/blog/benefits-of-low-pressure-overmolding. (Year: 2018).*

\* cited by examiner

*Primary Examiner* — Michael N Orlando
*Assistant Examiner* — Christopher W Raimund
(74) *Attorney, Agent, or Firm* — Banner & Witcoff, Ltd.

(57) ABSTRACT

A method of manufacturing an implantable stimulation device includes providing a circuit board of the implantable stimulation device, the circuit board being equipped with circuit components and an antenna, adhering one or more electrodes to the circuit board, and applying an insulation material to the circuit board such that the insulation material forms a housing that surrounds the circuit board, the circuit components, and the antenna, while leaving the one or more electrodes exposed for stimulating a tissue.

4 Claims, 28 Drawing Sheets

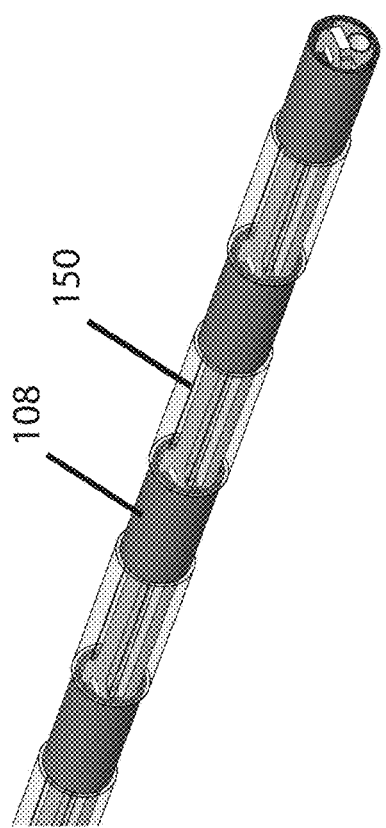
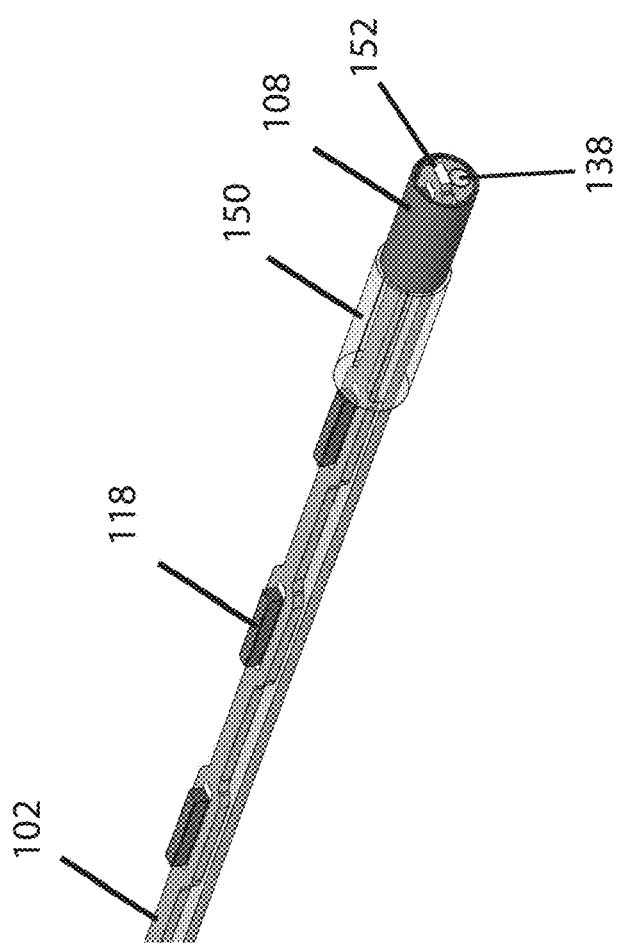
FIG. 8B
FIG. 8A

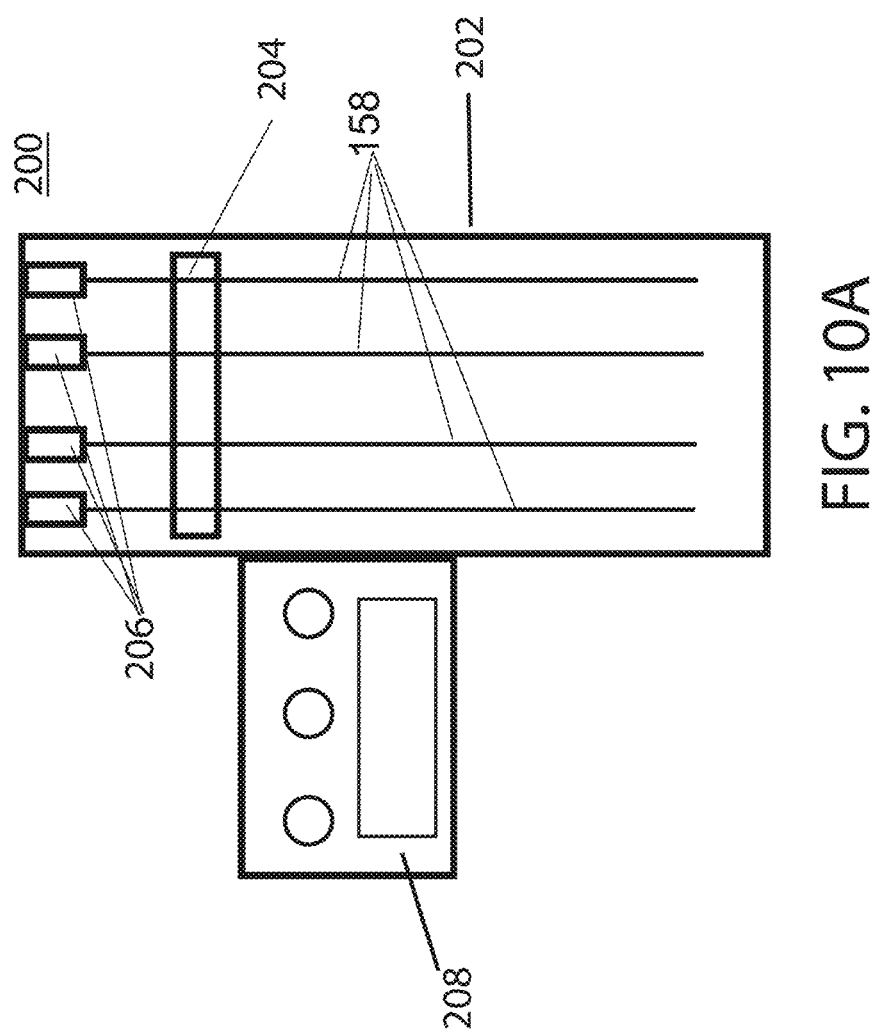

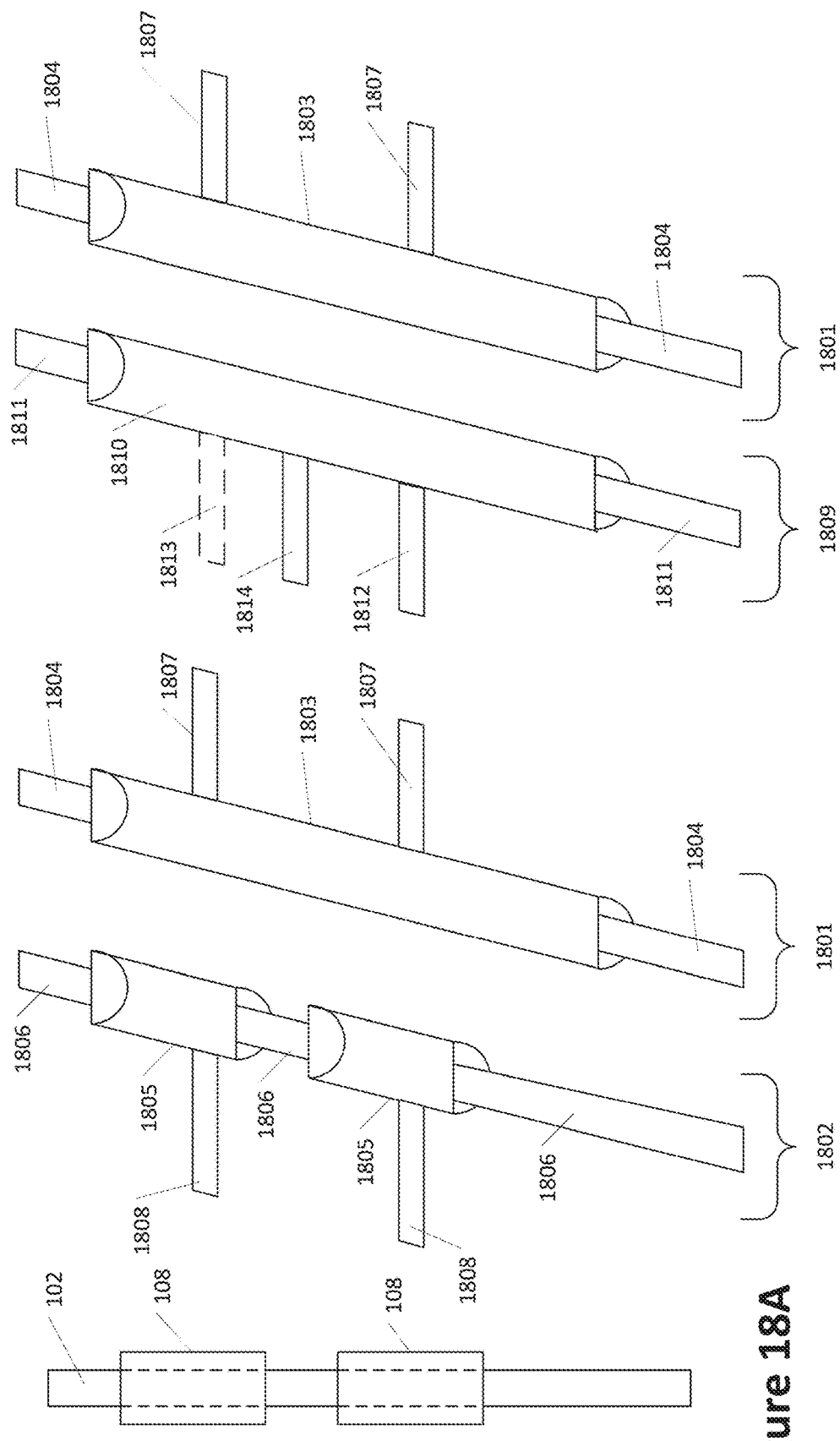

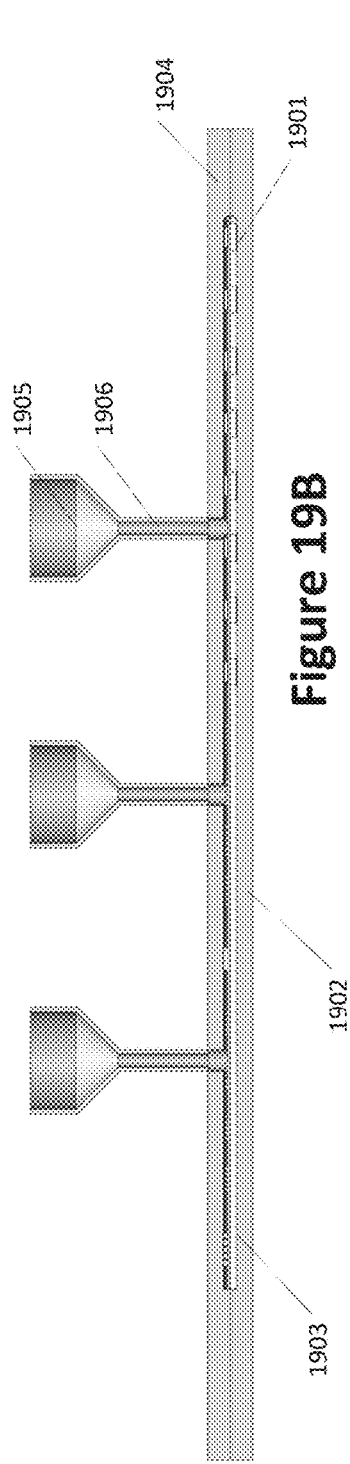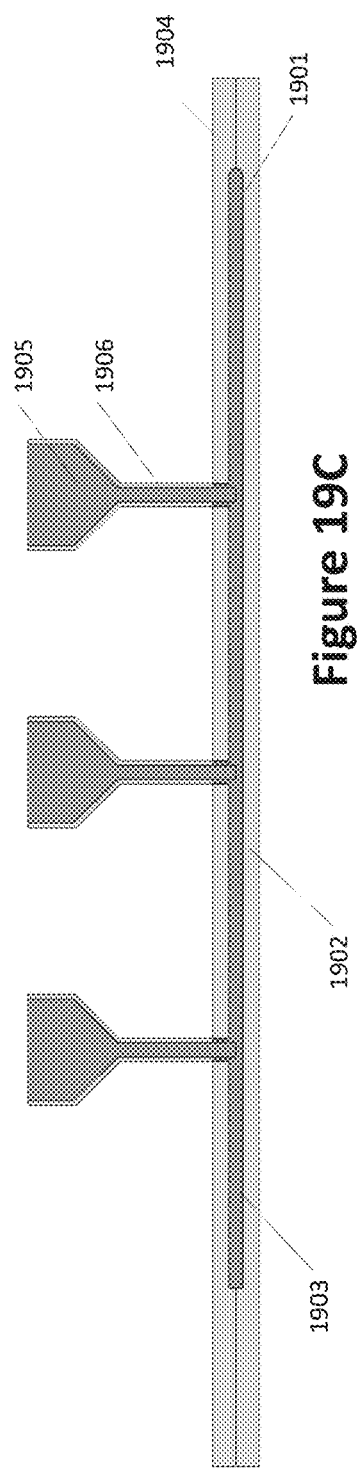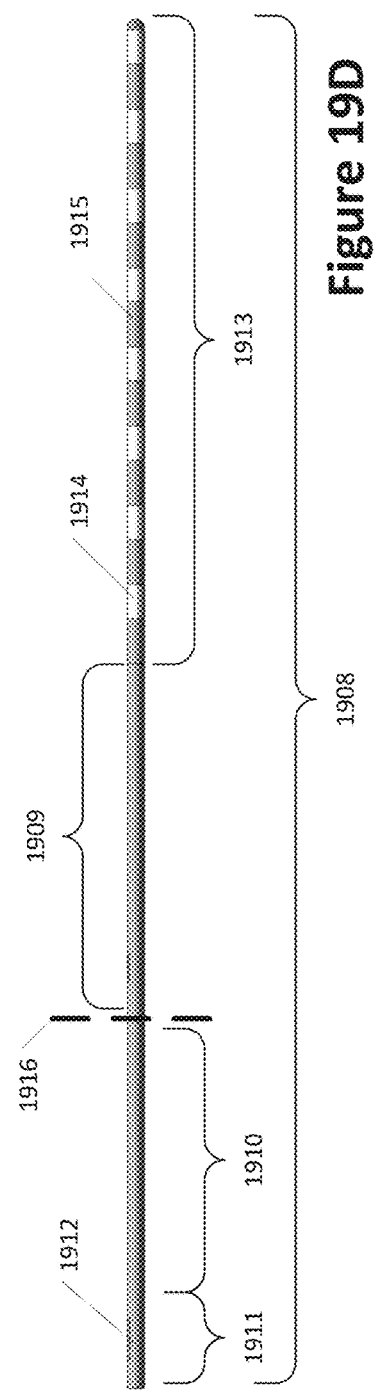

MANUFACTURING IMPLANTABLE TISSUE STIMULATORS

TECHNICAL FIELD

This disclosure relates to manufacturing implantable tissue stimulators using various overmolding techniques.

BACKGROUND

Modulation of tissue within the body by electrical stimulation has become an important type of therapy for treating chronic, disabling conditions, such as chronic pain, problems of movement initiation and control, involuntary movements, dystonia, urinary and fecal incontinence, sexual difficulties, vascular insufficiency, and heart arrhythmia. For example, an external antenna may be used to send electrical energy to electrodes on an implanted tissue stimulator that can pass, to the tissue, pulsatile electrical signals including one or more of controllable frequency, controllable pulse width, and/or controllable amplitudes.

SUMMARY

In general, this disclosure relates to methods of manufacturing implantable tissue stimulators, such as methods that incorporate injection molding or dip coating techniques.

In one aspect, a method of manufacturing an implantable stimulation device includes providing a circuit board of the implantable stimulation device, the circuit board being equipped with circuit components and an antenna, adhering one or more electrodes to the circuit board, and applying an insulation material to the circuit board such that the insulation material forms a housing that surrounds the circuit board, the circuit components, and the antenna, while leaving the one or more electrodes exposed for stimulating a tissue.

Additional aspects, configurations, embodiments and examples are described in more detail below.

DESCRIPTION OF DRAWINGS

Certain manufacturing techniques and manufactured devices are described below with reference to the accompanying figures.

FIG. 5A shows a laser welding technique. FIG. 5B shows a soldering technique. FIG. 5C shows a conductive epoxy application technique.

FIGS. 6A-6B, 7A-7B, 8A-8C, and 9 show a series of steps involved in manufacturing the tissue stimulator of FIG. 1 using extruded components.

FIG. 10A shows an example of a reflow oven that may be used to manufacture at least a portion of the tissue stimulator of FIG. 1.

FIG. 18A shows an example of a circuit board and electrodes before overmolding. FIG. 18B shows an example of two dies that together form a mold with a cavity having round and half-round cross-sections. FIG. 18C shows an example of two dies that together form a mold with a cavity having a round cross section.

FIG. 19B is a side view of the mold of FIG. 19A before overmolding of the insulating material. FIG. 19C is a side view of the mold of FIG. 19A with the insulating material filling the cavities of the mold. FIG. 19D shows an enlarged view of resulting tissue stimulator removed from the mold of FIG. 19C.

DETAILED DESCRIPTION

Certain improvements to processes for applying an insulator to a tissue stimulator are described. The various processes may include injection molding (e.g., using over molding or insert molding or a combination thereof) and/or heat treatment of a reflowable insulating material.

Figure 1:
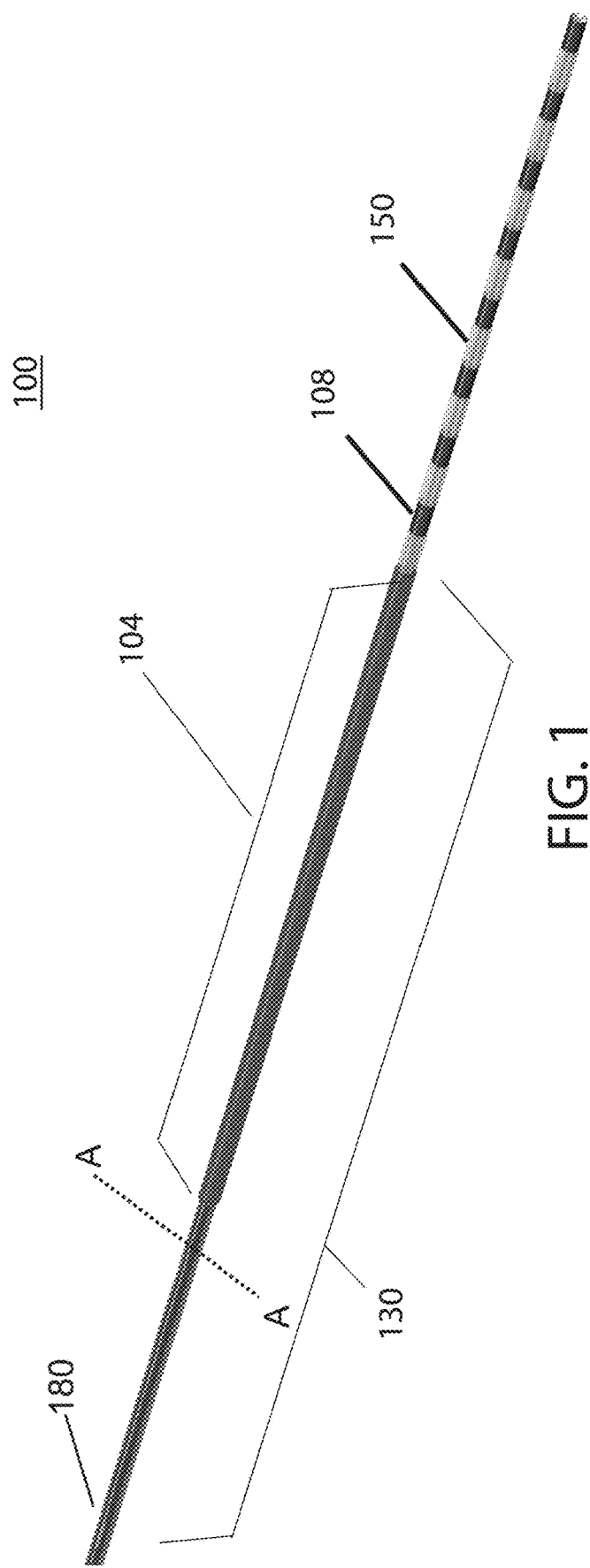
FIG. 1 is a perspective view of an example of tissue stimulator manufactured in part using an injection molding technique with extrusion components.
Figure 2:
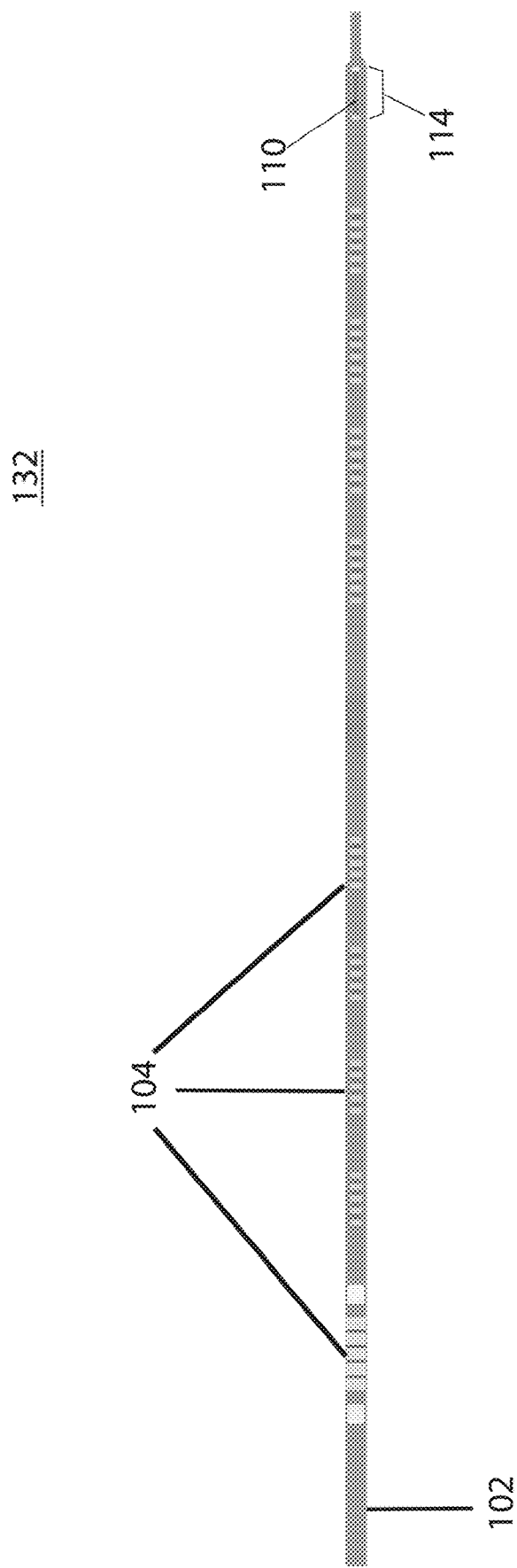
FIG. 2 is a top view of an electronic assembly of the tissue stimulator of FIG. 1.
Figure 3:
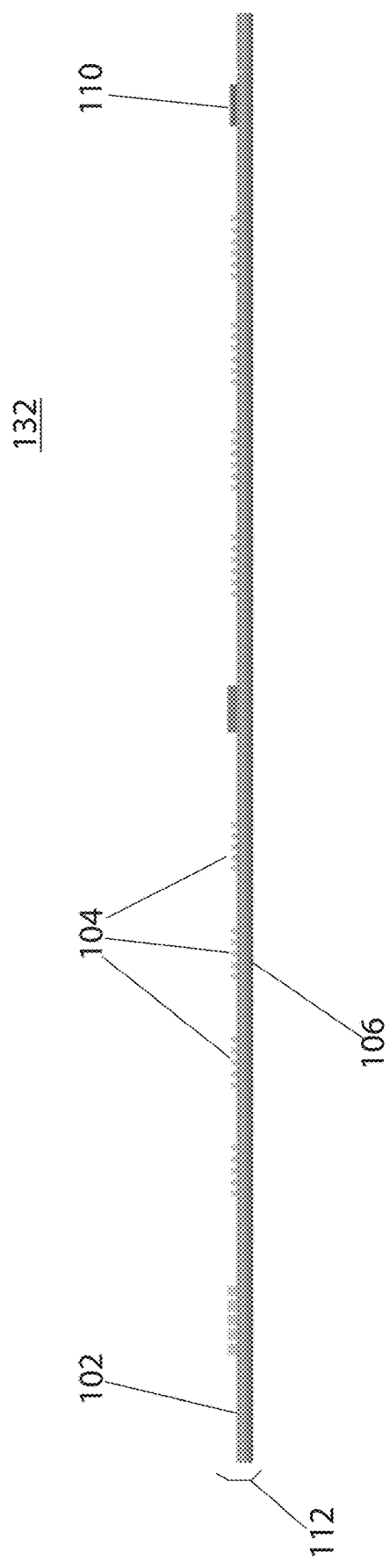
FIG. 3 is a side view of the electronic assembly of FIG. 2.

FIG. 1 shows an example of a tissue stimulator 100 configured to be implanted within a patient's body for delivering electrical therapy to tissues within the body. The tissue stimulator 100 may comprise an exterior design that provides strength and a smooth profile for optimal insertion and performance within the patient. For example, the tissue stimulator 100 may comprise a housing 130 that is molded (e.g., overmolded or insert molded) of a clear material (and/or opaque and/or translucent material) around various internal components of the tissue stimulator 100. Accordingly, the tissue stimulator 100 may be referred to as a monolithic device for which electronic components are secured to one small, flat substrate that may be delivered to the body through an introducer needle. Referring to FIGS. 1-3, the tissue stimulator 100 may further comprise a circuit board 102, various circuit components 104, an antenna 106, and electrodes 108 that are secured to the circuit board 102. Spacers 150 may be also secured to the circuit board, where the spacers 150 are arranged alternately with the electrodes 108. The tissue stimulator 100 further comprise multiple contact pads 110 at which the electrodes 108 are respectively attached to the circuit board 102.

The circuit board 102 may comprise a flexible substrate having multiple layers 112 in which the antenna 106 is interposed. The circuit board 102 defines contact sites 114 that locate the contact pads 110. The contact pads 110 may be platinum or other high conductivity metal (e.g., gold, silver, or an alloy). The circuit board may typically have a length of about 0.5 mm to about 450 mm, a width of about 0.05 mm to about 2.0 mm, and a thickness of about 0.125 mm to about 1.0 mm. For reference, the term "about" may mean±20%. Other values of ±30% or ±40% may also be used. The circuit board 102 may comprise a dielectric substrate, such as polyimide. In some embodiments, additional dielectric materials may be applied to the circuit board 102 at or along certain regions for stiffening.

The circuit components 104 may be distributed along the length of the circuit board 102 and may be secured to the circuit board 102 via one or more of solder, solder paste, or conductive epoxy. Examples of circuit components 104 may include one or more of diodes, capacitors, resistors, semiconductors, or other electromechanical components. The antenna 106 may be integrated directly into one of the layers 112 of the circuit board 102. Alternatively or additionally, at least a portion of the antenna 106 may be separate from the circuit board 102. Further the antenna 106 may be integrated into two or more layers 112 of the circuit board 102. The antenna 106 may be configured to receive an input signal carrying electrical energy. The received electrical energy may be used by the circuit components 104 with at least a portion of the received electrical energy relayed to the electrodes 108. The portion of the electrical energy transmitted (e.g., as pulses) to the electrodes 108 may be provided, via the electrodes 108, to adjacent tissue. Arrangement of the antenna 106 along a layer 112 contributes to a compact and simplified structure of the tissue stimulator 100 in that such configuration avoids the need for additional cables or attachment features to electrically connect a separate antenna 106 with the circuit components 104. In some embodiments, the tissue stimulator 100 may include one or more additional trace pathways to serialize the circuit components 104 and render the tissue stimulator 100 viewable with standard imaging equipment (e.g., X-ray equipment). For example, the circuit board 102 may include one or more built-in coupling traces that may extend a transmission zone of the tissue stimulator 100. Such coupling traces may or may not be directly connected to the primary circuit components 104 (e.g., as in the case of near field RF coupling). An electronic assembly 132 including a circuit board 102 that is equipped with circuit components 104, an antenna 106, and layers 112 may be manufactured individually or in an array of individual electronic assemblies 132 as part of a mass production process.

Figure 4:
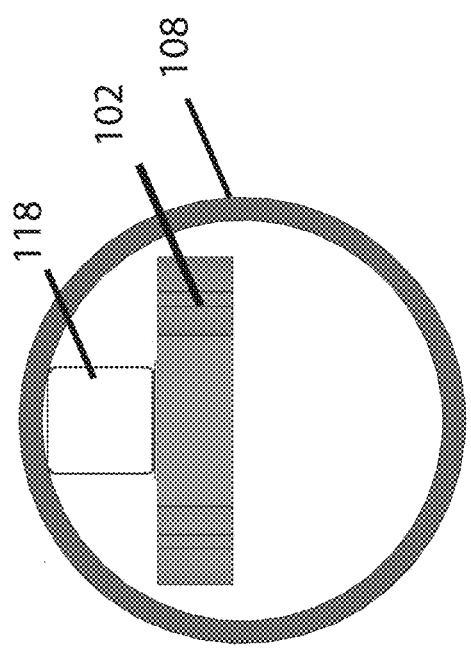
FIG. 4 is a side cross-sectional view of a circuit board of the electronic assembly of FIG. 2 with electrodes attached thereto.

The electrodes 108 may have a generally cylindrical shape that may be secured to the contact pads 110 at the contact sites 114. The electrodes 108 may be attached to the contact pads 110 via one or more of physically mating, welding, soldering, or gluing (e.g., using epoxy as a glue). The electrodes 108 typically have a length of about 0.5 mm to about 6 mm and an internal diameter of about 0.9 mm to about 1.5 mm. Referring to FIGS. 2 and 4, the electrodes 108 may be attached to the contact sites 114 and around the circuit board 102, electrically connected to contact pads 110 via the contact joints 118. The contact joints 118 extend along longitudinal axes 120 of the electrodes 108. The contact joints 118 provide additional surface area at which the electrodes 108 may be attached. The electrodes 108 and the contact joints 118 may be made of one or more biocompatible materials (e.g., noble metals or other metals) that have good conductivity characteristics and result in a good tissue response, such as stainless steel, platinum, platinum-iridium, gallium-nitride, titanium-nitride, iridium-oxide, or other materials (e.g., silver, gold, rhodium, palladium, ruthenium, osmium, or rhenium). The contact joints 118 may have, for example, a circular cross-sectional or otherwise rounded shape, presenting an outer surface to which the electrodes 108 may be attached. Furthermore, the contact joints 118 may serve as fiducial markers (e.g., radio-opaque markers or other types of visual markers). Additionally, the combination of contact joints 118 and electrodes 108 together may serve as fiducial markers. For instance, to serve as markers that show (e.g., as seen on via radiographic imaging) a far end of the tissue stimulator, additional, unpowered electrodes 180 (and possibly additional spacers) may be placed at an opposite end of the circuit board from the electrode 108/spacers 150.

In some embodiments, the contact joints 118 may be attached to the circuit board 102 at the contact sites 114 in an automatic manner (e.g., via surface mount techniques that utilize tape and reel machine mechanisms) at a high production rate with reduced labor. In some embodiments, the contact joints 118 may be soldered to the circuit board 102 by hand. The contact joints 118 may have a thickness of about 0.05 mm to about 0.5 mm and may have a length that is slightly shorter than the respective electrodes 108. The circuit board 102 and the contact joints 118 are sized, dimensioned, and arranged to promote filing of cavities with insulation material that forms the housing 130 during manufacturing of the tissue stimulator 100, as will be discussed in more detail below. Dashed line A-A of FIG. 1 may represent, in some examples, where two separate circuit boards are joined together using wires and/or cables, thereby providing enhanced flexibility the tissue stimulator 100.

Figure 5C:
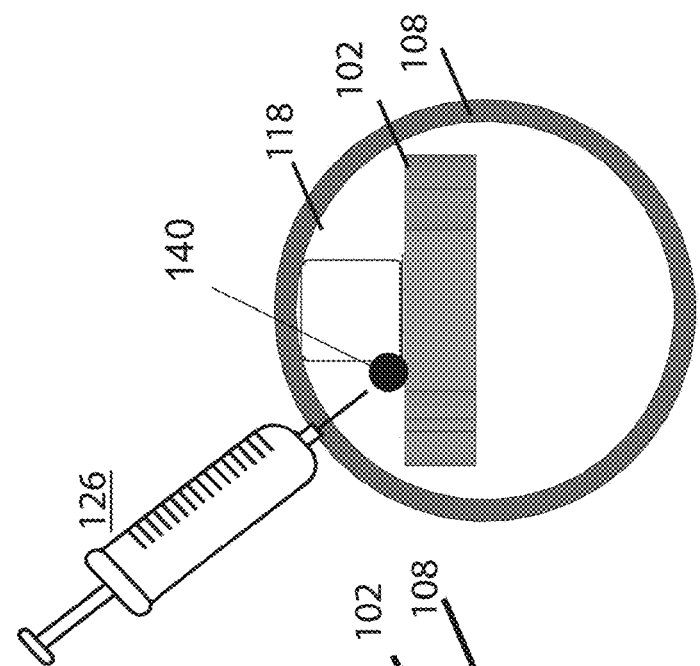
FIGS. 5A-5C show various techniques by which the electrodes of FIG. 4 may be attached to the circuit board of FIG. 4.
Figure 5B:
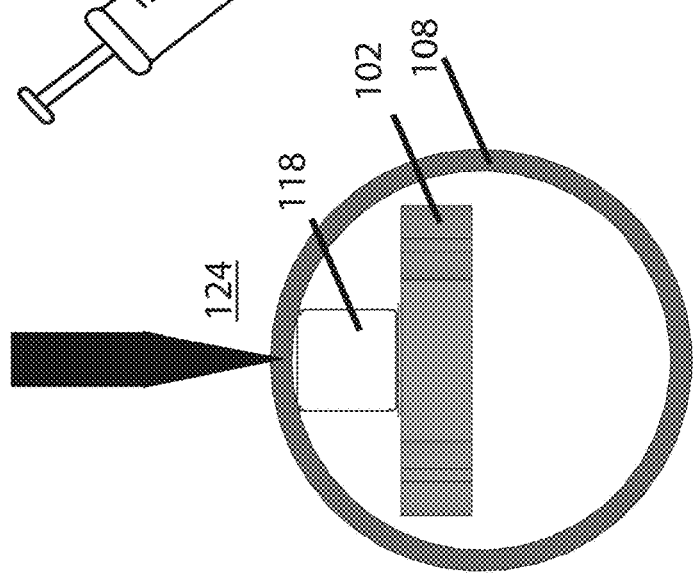
Figure 5A:
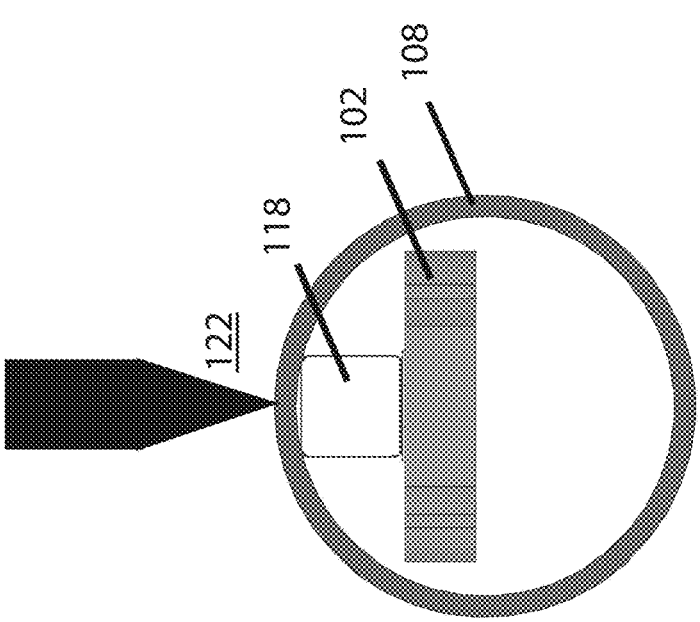

Referring to FIGS. 5A-5C, the electrodes 108 may be attached to the circuit board at the contact joints 118 using various attachment techniques, such as laser welding, soldering, or conductive epoxy application (e.g., chemical bonding) or combinations thereof. Such techniques may be carried out automatically using computer controlled processing heads (e.g., via a laser head 122 of FIG. 5A, via a soldering tip 124 of FIG. 5B, or via a syringe 126 applying epoxy 140 of FIG. 5C). The processing heads may be controlled to attach multiple electrodes 108 to the contact joints 118 on the circuit board 102 in one pass or in multiple passes. In this manner, the electrodes 108 may be attached to the circuit board 102 in a uniform manner within specified tolerances and without cables (e.g., stainless steel wires, braided wires, or other wires) extending along the circuit board 102 and between the electrodes 108. In contrast, including separate cables may require manual assembly to align the cables between the electrodes 108 and the circuit board 102. Referring to the structures of FIGS. 4 and 5A-5C, in some embodiments, the electrodes 108 may be slid over the circuit board 102 and positioned at the contact joints 118 as part of the laser welding, soldering, or epoxy techniques discussed above. For example, a microscope with optical tweezers or other specialty tooling and equipment may be used to position the electrodes 108 along the circuit board 102.

As compared to conventional implantable electronic devices for which electrodes are secured to a circuit board via multiple cables, the tissue stimulator 100 may be more easily assembled (e.g., automatically and more quickly at a lower cost), more flexible, may withstand greater bending forces (e.g., avoiding the problem of cables popping off of electrodes), is more mechanically robust within a moving body, and is therefore less likely to fail mechanically. Additionally, the electrodes 108 may be assembled more uniformly with respect to positional accuracy and mechanical integrity, as compared to electrodes that are manually secured to a circuit board with multiple cables.

In some embodiments, an overall footprint and three-dimensional shape of the tissue stimulator 100 may be selected to provide optimized electrical and mechanical performance of the circuit components 104 and the electrodes 108, provide minimal tissue contacting surface areas, and/or provide an anchoring structure that prevents or reduces movement of the tissue stimulator 100 within the body. With respect to an anchoring structure, protrusions or barbs may be used to help secure the tissue stimulator 100 once inserted into a body.

Figure 6B:
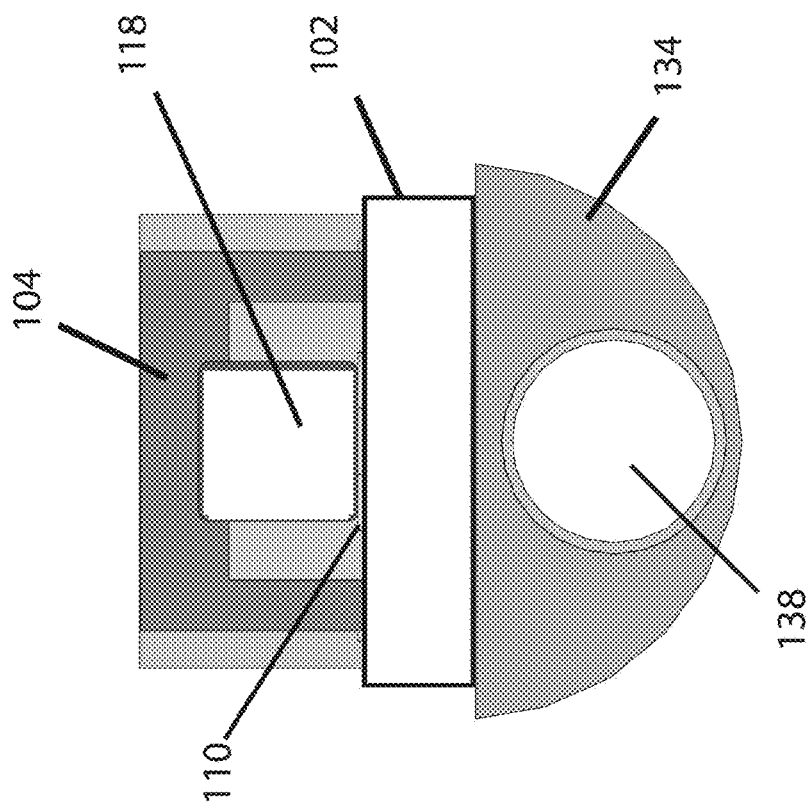
Figure 6A:
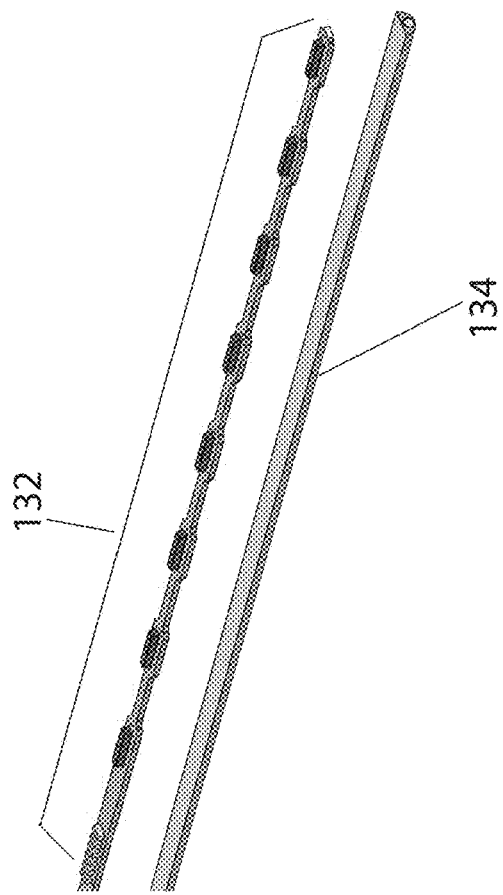

FIGS. 6A-6B, 7A-7B, 8A-8C, and 9 show various views of a tissue stimulator 100 during various stages of manufacturing using, for example, extruded components. Referring to FIGS. 6A and 6B, the electronic assembly 132 is placed atop a lower extruded component 134. The lower extruded component 134 may comprise an elongate component that extends a length at least as long as the length of the circuit board 102. The lower extruded component 134 may have a generally semi-circular outer cross-sectional shape and may comprise a flat recessed surface 136 for supporting the circuit board 102. The lower extruded component 134 may include an interior through-channel 138 that is sized to allow passage of ancillary surgical equipment, such as a steering stylet, a rigidity stylet, and/or an implantable receiver, etc. The lower extruded component 134 typically has a length of about 1 cm to about 38 cm and a maximum width (e.g., a diameter) of about 0.5 mm to about 2.0 mm. The interior through-channel 138 typically has a diameter of about 0.2 mm to about 1.0 mm.

Figure 7B:
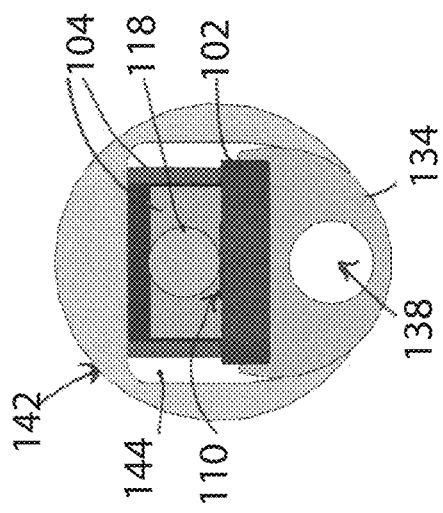
Figure 7A:
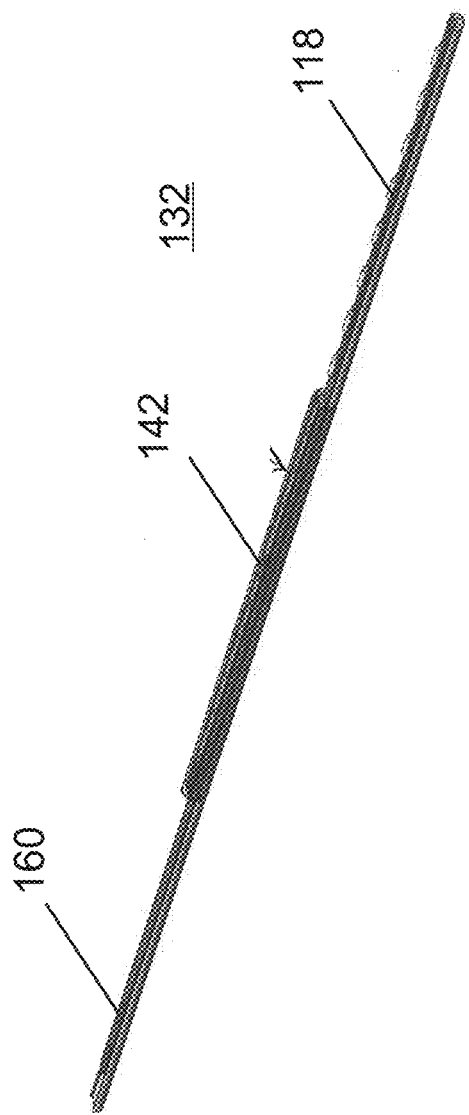

Referring to FIGS. 7A and 7B, an upper extruded component 142 is placed atop the electronic assembly 132 (e.g., over the circuit components 104) while the electronic assembly 132 is supported on the lower extrusion component 134. The upper extruded component 142 may comprise an elongate component that extends a length of about 1 cm to about 30 cm to protect the circuit components 104. The upper extruded component 142 may have a generally round (e.g., circular, oval, elliptical, including regular and irregular versions of each) outer cross-sectional shape through at least most of its periphery and may comprise a generally rectangular channel 144 that is sized to fit over the circuit components 104 and the width of the lower extruded component 134. Both the lower and upper extruded components 134, 142 may be made of polyurethane or other flexible polymers such as carbothane, pellethane, silicone, or thermoplastic polyurethane (TPU).

In some embodiments, a tissue stimulator that is similar in construction and function to the tissue stimulator 100 may not be formed using the upper extruded component 142 and may instead be formed with a cylindrical tube that has an inner diameter fitting around the outer diameter of the electronic assembly 132, such that the electronic assembly 132 is inserted into the cylindrical tube.

Figure 8C:
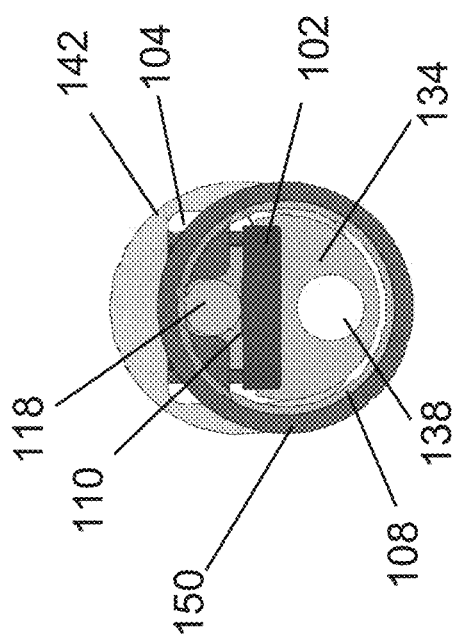

Referring to FIGS. 8A, 8B, and 8C, the electrodes 108 and the spacers 150 may be slid over and positioned along the electronic assembly 132 at contact sites 114. For example, an electrode 108 may be attached to a contact joint 118 in an automated manner via any of techniques discussed above with respect to FIGS. 5A-5B. A spacer 150 may be slid over and positioned adjacent to the attached electrode 108. For example, the spacers 150 may be placed on the electronic assembly 132 using an automated arm and/or conveyor that slides the spacers 150 into position and then welds the spacers 150 in place. The spacer 150 may include a circular outer cross-sectional shape and an inner cross-sectional shape, with the inner cross-sectional shape to pass over the lower extruded component 134 and the contact joints 118 attached thereto. The spacers 150 typically have a length of about 0.5 mm to about 6 mm and an internal diameter of about 0.2 mm to about 1.5 mm. The spacers 150 may be made of materials that may reflow when heat is applied to create a water-tight seal against surrounding components, such as the components of the electronic assembly 132. For example, the spacers 150 may be made of flexible biocompatible polymers, such as polyurethane, pellethane, carbothane, or silicone. Another electrode 108 may be positioned against a free end of the spacer 150 and attached to a respective contact joint 118, and the remaining spacers 150 and electrodes 108 may be assembled along the circuit board 102 in a like manner, in an alternating arrangement.

Figure 9:
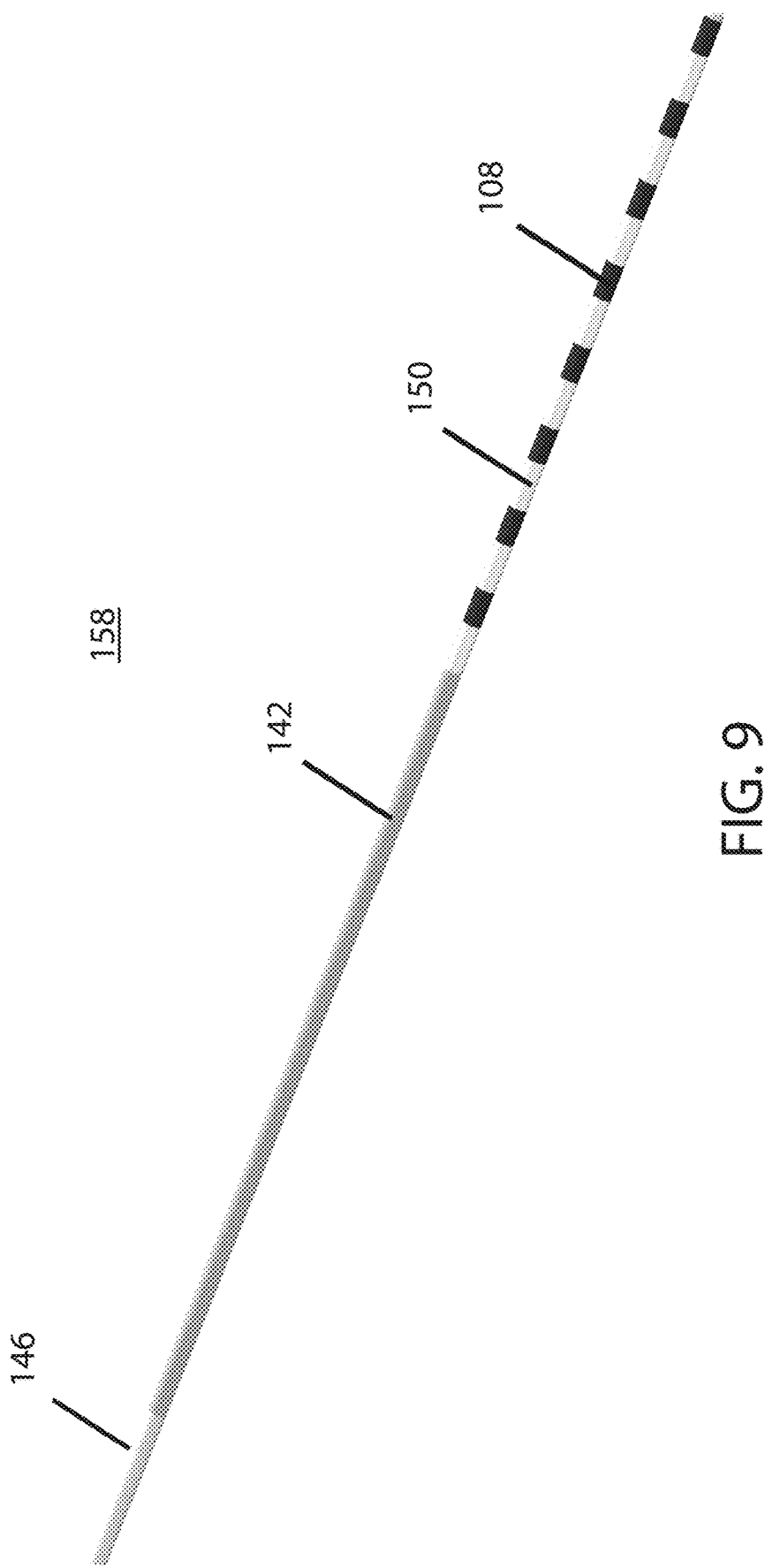

Referring to FIG. 9, an extended housing component 146 is slid over the circuit board 102 and positioned at an end of the circuit board 102 that is opposite the electrodes 108. The extended housing component 146 typically has a length of about 1 mm to about 450 mm and an internal diameter of about 0.2 mm to about 1.5 mm. The housing component 146 may be made of the same material from which the spacers 150 are made or another non-reactive material. When all of the spacers 150 and the housing component 146 are made of the same polymer material, the spacers 150 and the housing component 146 may be fused together during a single heating process to provide the strong, durable bonds. The assembly 158 as shown in FIG. 9 may be placed in a reflow oven, where a piece of heat shrink tube (not shown) is placed around the entire assembly 158 and is flowed over an entire length of the assembly 158. Once the entire assembly 158 is reflowed, the heat shrink tube is cut and peeled off of the assembly 158 to form the tissue stimulator 100 as shown in FIG. 1 The interior through-channel 138 may extend the full length of the tissue stimulator 100.

Figure 10B:
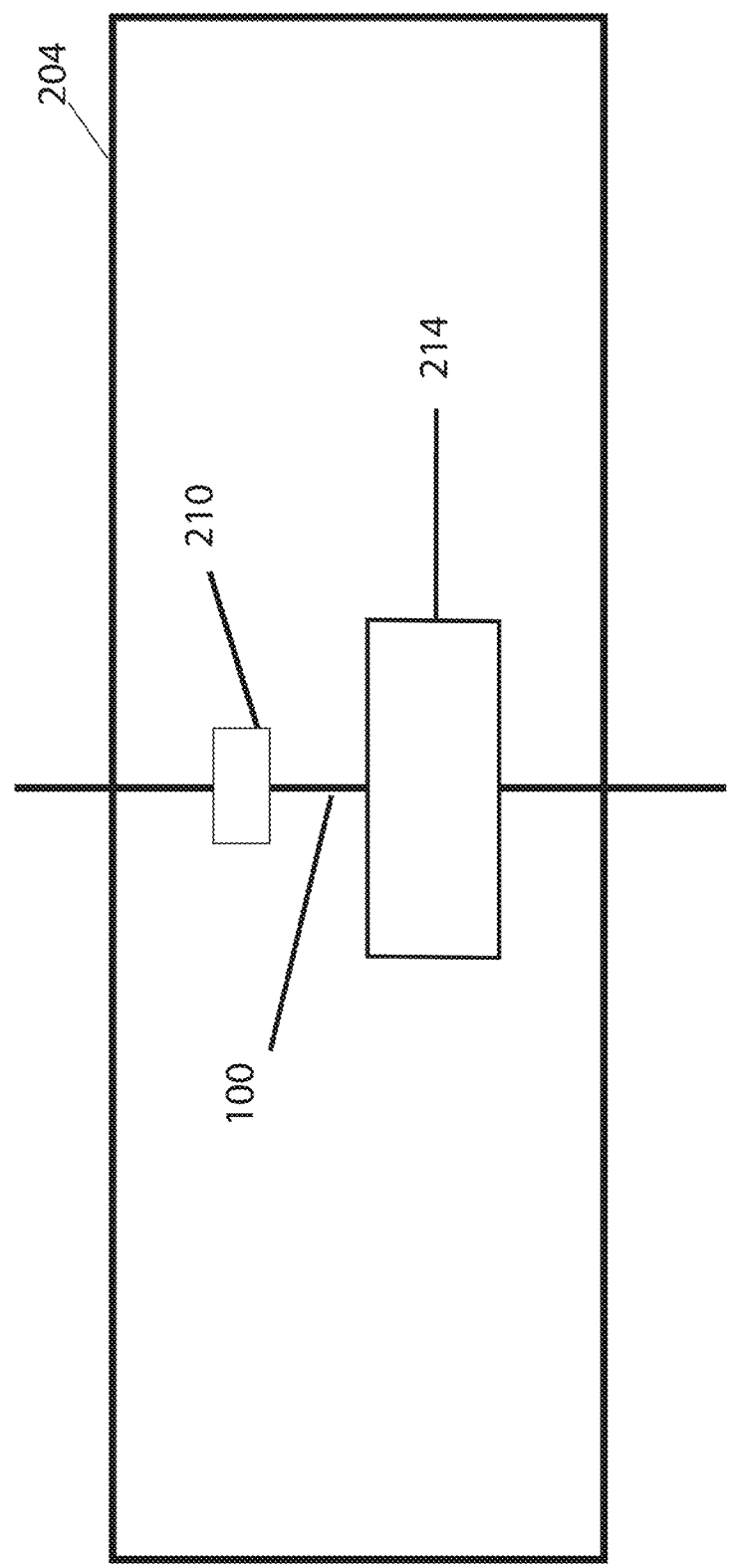
FIG. 10B shows an enlarged view of a portion of the reflow oven of FIG. 10A.

FIG. 10A shows an example reflow oven 200 that may be used to perform the heating process fusing the spacers 150 and housing component 146 described in relation to FIG. 9. In FIG. 10A, the reflow oven is shown in a tower-type footprint. Other footprints may be used and the fusing process varied depending on the type of heating operation used (e.g., batch processing, continuous processing, or a combination thereof). The reflow oven 200 includes a support frame 202, a heating element shuttle 204 that is translatable vertically along the support frame 202, and multiple (e.g., four or as provided) clamps 206 that are configured to grasp components including, but not limited to, mandrels, tissue stimulators 100, catheters, or other products. In the example of FIG. 10A, the grasped components may remain stationary while the heating element shuttle 204 moves along the length of the grasped components. Additionally or alternatively, a heating element may remain stationary while the components to be heated move past the heating element. Further, the heating process may be part of a larger batch heating operation in which all components are loaded into a reflow oven, simultaneously heated, then removed. Other variations may be used as well. The reflow oven 200 may also include a control panel 208 by which several parameters (e.g., speed, timing, and temperature) may be controlled for each of the grasped components. The control panel 208 may include one or more displays that identify various parameters to be applied to a heating operation FIG. 10B is an enlarged view of the heating element shuttle 204. Shown in FIG. 10B is a stabilizing clamp 210 (made of plastic or another material), a heater band 214, and the tissue stimulators 100. The tissue stimulators 100 are stationary, and the heating element shuttle 204 moves along the length of the tissue stimulators 100 as governed by parameters. The parameters may be entered by a user, previously stored in a memory accessible by the control panel 208 (e.g., a local memory, a remote memory, or a combination of memory local to the control panel and remote from the control panel 208). As desired, the parameters may be fixed before the heating process begins or may be adjusted during the heating process to account for variations in materials, humidity, and/or other variables).

To prepare an assembly 158 for fusing, the assembly 158 may be wrapped in a heat shrink material. Additionally or alternatively, the assembly 158 may be slid into the heat shrink tube. The assembly with the surrounding heat shrink material is clamped with clamp 210. A coated mandrel (e.g., coated with polytetrafluoroethylene) is slid into through-channel 138 of the assembly 158. In this example, the assemblies 158 are hanging vertically downward from clamps 210. Alternatively, the clamps 210 may be positioned vertically below the assemblies 158. Further, the clamps may be placed on a side and the assemblies held horizontally or at another angle. The clamps may not move relative to the reflow oven 200 or may rotate the assemblies and/or relative to the reflow oven to minimize the heat shrink material from pooling about one side or end of the assemblies 158. When the reflow process is initiated, the precise, temperature-controlled heating element shuttle 204 traverses the length of the assembly 158 to reflow the polymer material of the spacers 150 and the housing component 146 to join them together, thereby unifying the assembly 158 section-by-section.

Figure 11A:
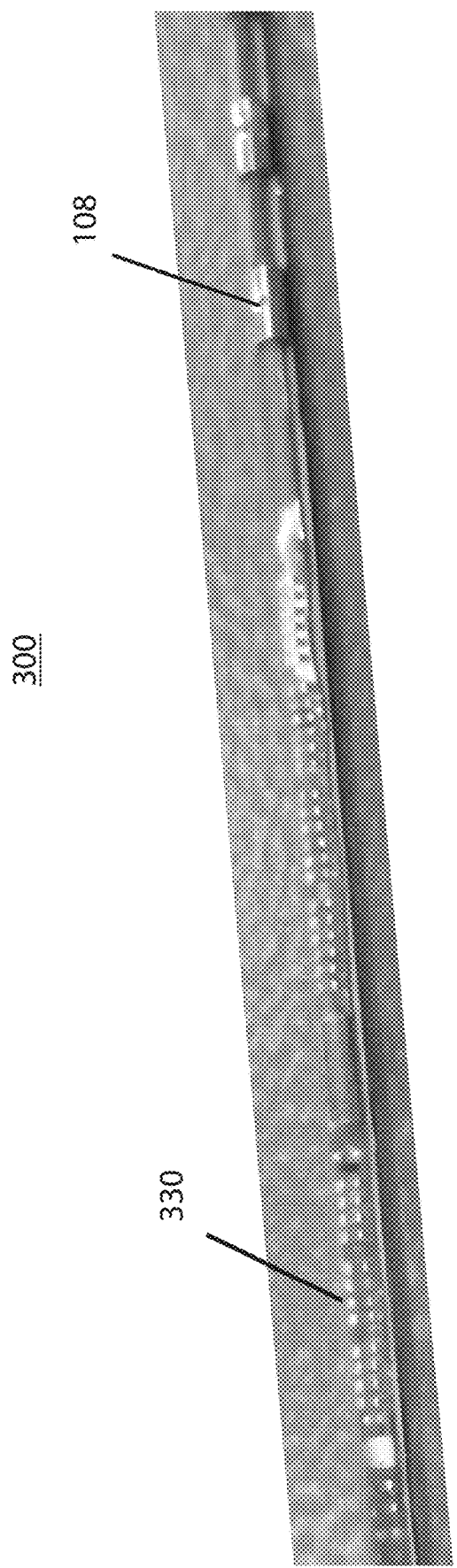
FIG. 11A is a perspective view of a tissue stimulator manufactured in part using an injection molding technique with a silicone material.

In some embodiments, a tissue stimulator that is similar in construction and function to the tissue stimulator 100 may be manufactured via overmolding with a different material, such as silicone. FIG. 11A is an example of such a tissue stimulator 300 that is substantially similar in construction and function to the tissue stimulator 100, except that a housing 330 of the tissue stimulator 300 is formed from a different insulation material, such as liquid silicone rubber. The tissue stimulator 300 includes, as described above, the circuit board 102, various circuit components 104, the antenna 106, and electrodes 108 that are secured to the circuit board 102. In lieu of spacers 150 of other examples, spaces between the electrodes 108 are filled, during the overmold process, with the liquid silicone rubber. Accordingly, the tissue stimulator 300 does not include the spacers 150. Alternatively or additionally, the tissue stimulator 300 may include at least one spacer 150 separating a first pair of electrodes but also include the silicone rubber separating another pair of electrodes. Additionally or alternatively, the spacers 150 may separate the electrodes as described above but also permit the silicone rubber to fill any gaps between the spacers 150 and electrodes 108. The tissue stimulator 300 may also include multiple contact pads 110 at which the electrodes 108 are respectively attached to the circuit board 102, as discussed above with respect to the tissue stimulator 100.

Figure 11B:
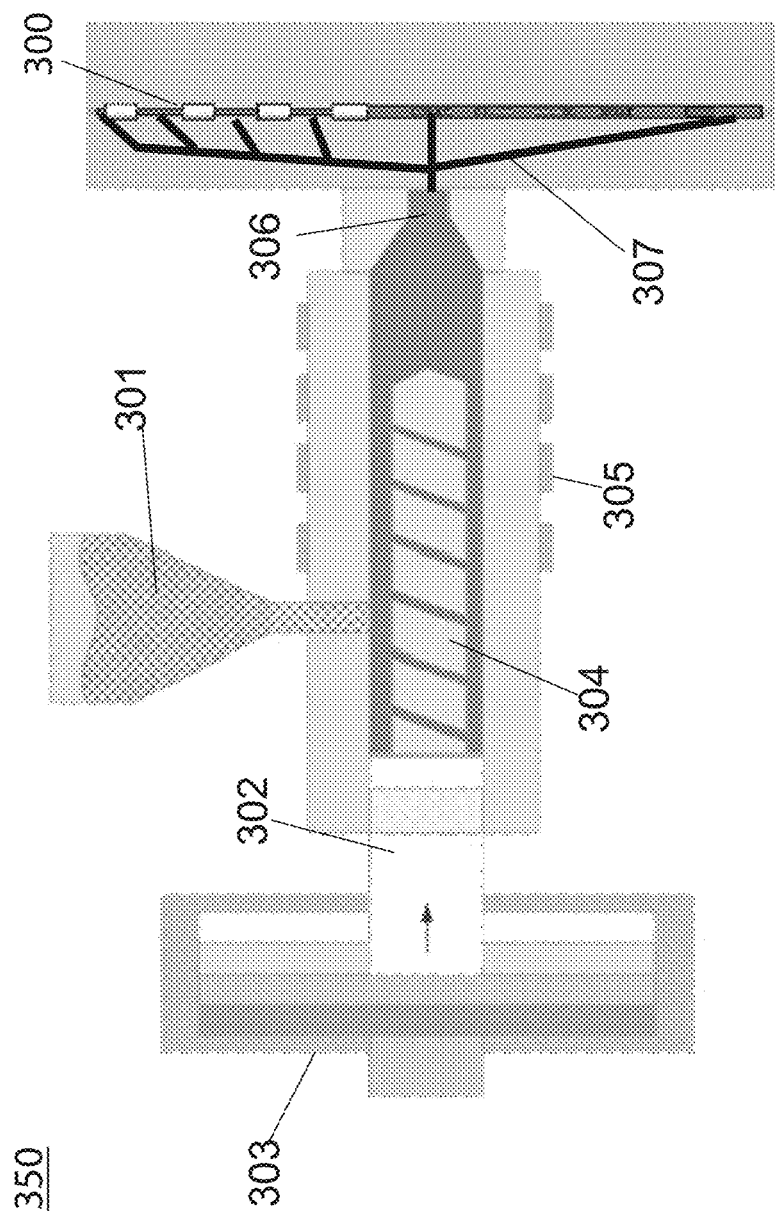
FIG. 11B shows an example injection mold that may be used to manufacture the tissue stimulator of FIG. 11A before flowing of the insulating material.
Figure 11C:
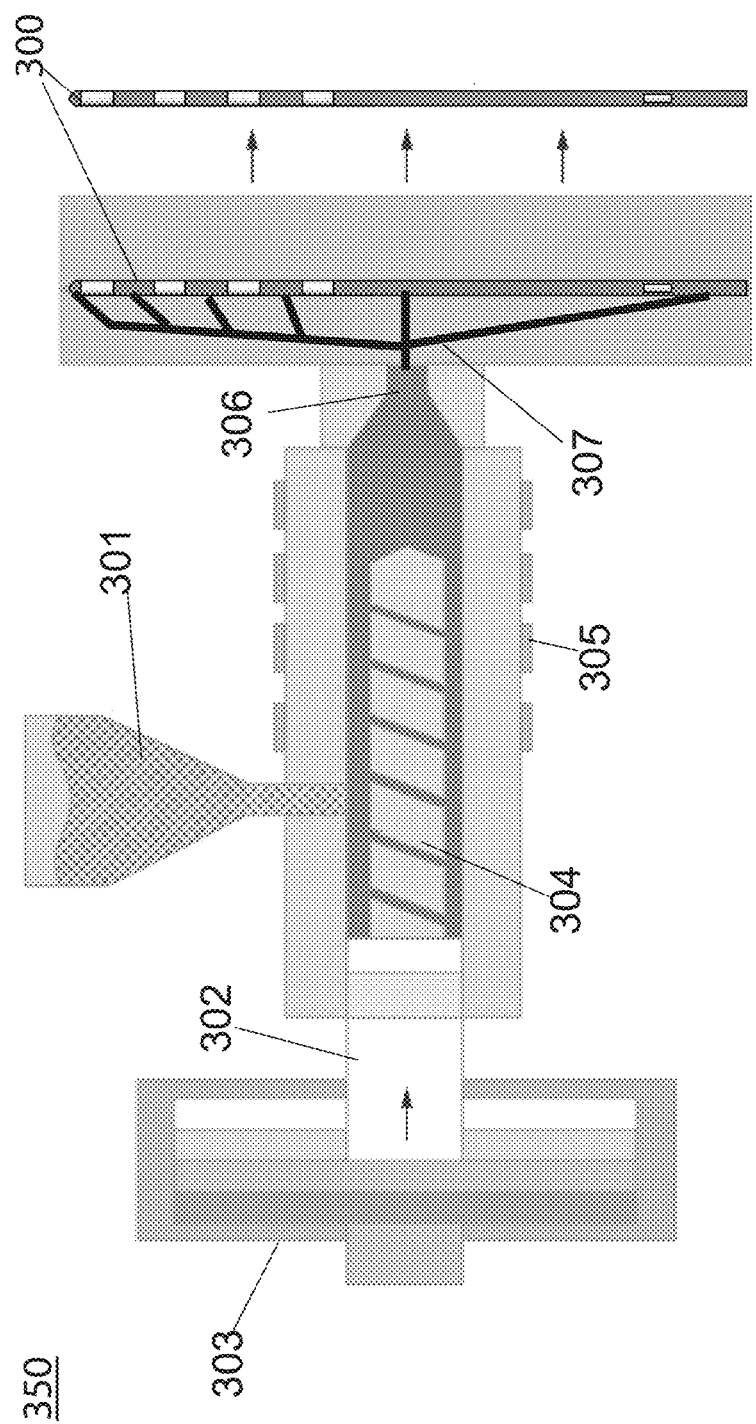
FIG. 11C shows the example injection mold of FIG. 11B after flowing of the insulating material.

FIG. 11B is an example of an injection mold 350 (e.g., comprising one or more cavities) that may be used to manufacture the tissue stimulator 300. In some embodiments, the tissue stimulator 300 may be manufactured by placing, inside of the injection mold 350, an assembly of the circuit board 102, equipped with the circuit components 104, the antenna 106, and the electrodes 108. The tissue stimulator 300 may be integrated, into a cylindrical shape, by encasing the components of the tissue stimulator 300 in the insulation material. For example, the insulation material may be injection molded using one or more of injection molding techniques including injection molding under high pressure, injection molding under low pressure, or injection molding using gravity to transport the insulating material into injection mold 350. The injection mold may be configured to only encase portions of the tissue stimulator 300 and not to cover at least portions of the electrodes 108 as electrodes 108 are intended to directly contact a patient's tissue. The injection mold 350 may have different widths for a channel along its length to permit the insulation material to flow over portions of the tissue stimulator 300 not proximate to the electrodes 108 and not flow over portions of the tissue stimulator 300 proximate to the electrodes 108 (e.g., by not permitting enough space around the electrodes 108 for the insulation material to pass). Alternatively or additionally, the injection mold 350 may restrict the flow of the insulation material to the electrodes. Alternatively or additionally, the assembled size of the circuit board 102, circuit components 104, antenna 106, and electrodes 108 may be narrower around the non-electrode portions of the tissue stimulator 300 while wider around the electrode portions of the tissue stimulator 300, the effect being that injection of the insulating material is able to encase the non-electrode portions while leaving the electrodes exposed. For example, one or more sprues may permit the insulating material to enter cavities between the electrodes. In some embodiments, the mold may have cavities that extend perpendicular to the tissue stimulator 300 to form fixation features (e.g., tines and/or barbs) on the housing 130 that provide a tissue-anchoring capability to the tissue stimulator 300 (e.g., by engaging with surrounding tissue to prevent relative movement between the tissue and the tissue stimulator 300).

Figure 12:
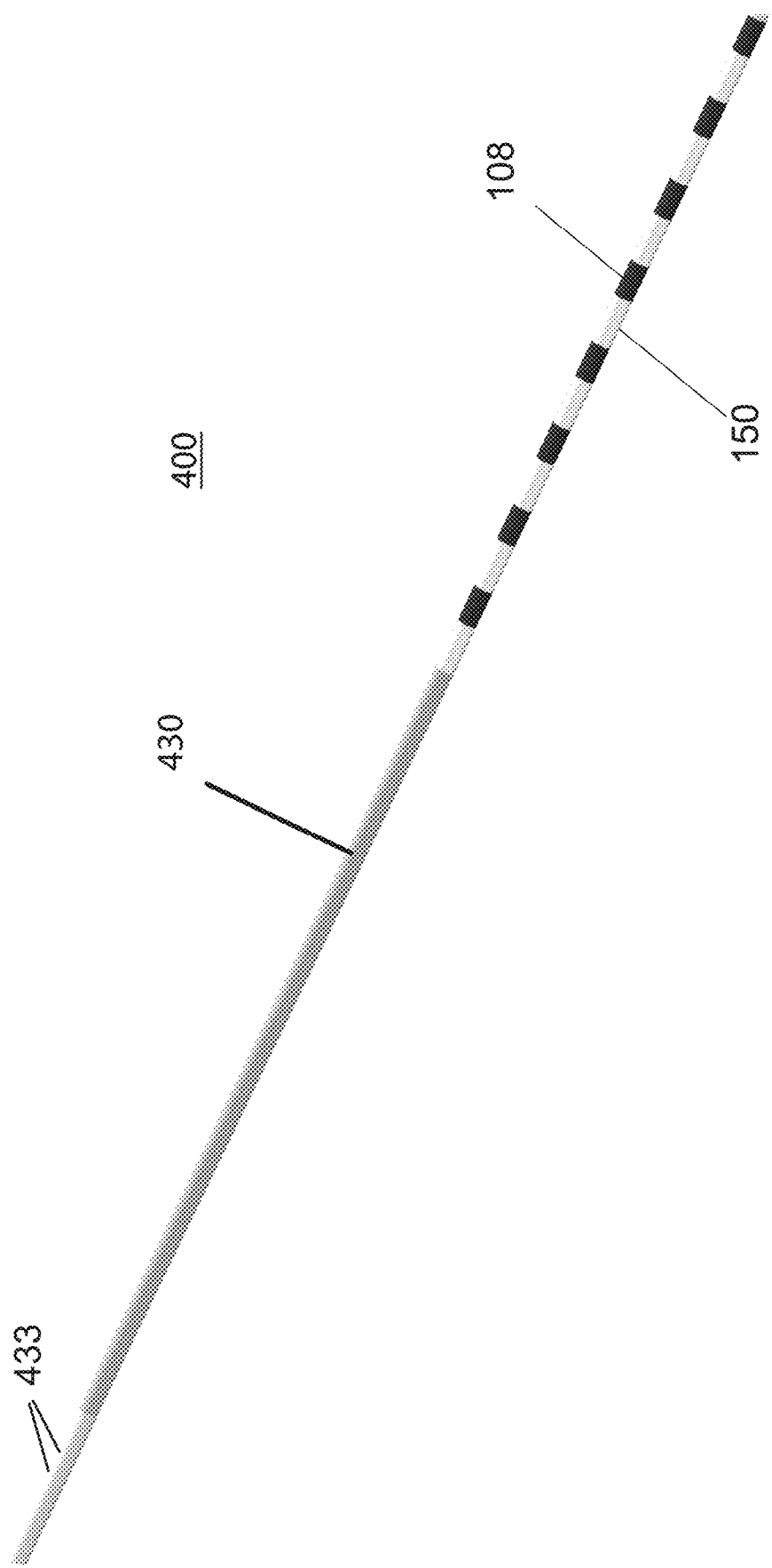
FIG. 12 is a perspective view of a tissue stimulator manufactured in part by dip coating.

In some embodiments, a tissue stimulator that is similar in construction and function to the tissue stimulator 100 may be manufactured using a dip coating process. For example, FIG. 12 shows such a tissue stimulator 400 that is substantially similar in construction and function to the tissue stimulator 100, except that a housing 430 of the tissue stimulator 400 and spacers 150 between electrodes 108 are formed by dip coating. Accordingly, the tissue stimulator 400 further includes a circuit board 102, various circuit components 104, an antenna 106, electrodes 108 that are secured to the circuit board 102, and multiple contact pads 110 at which the electrodes 108 are respectively attached to the circuit board 102, as discussed above with respect to the tissue stimulator 100.

Figure 13:
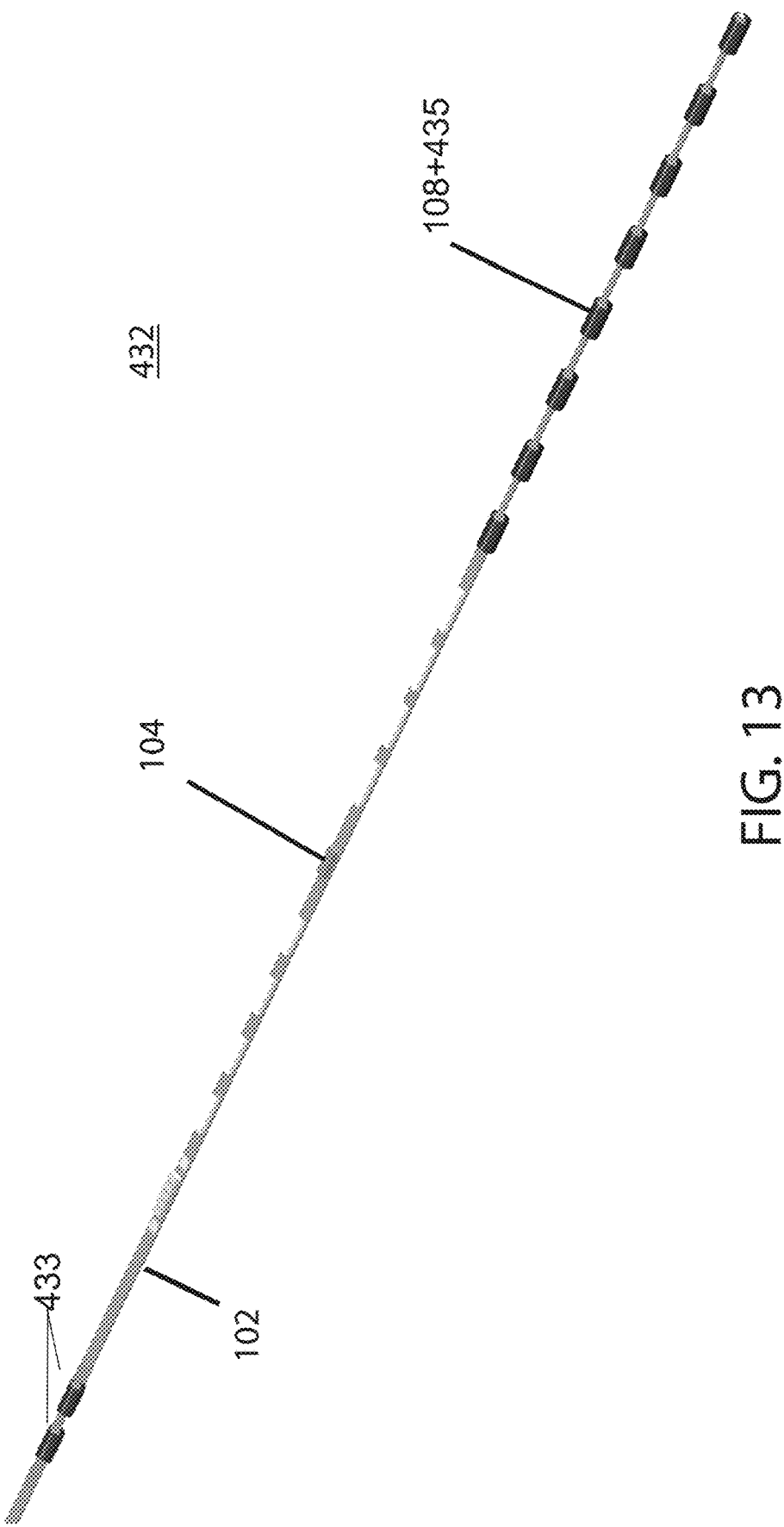
FIG. 13 is a subassembly of the tissue stimulator of FIG. 12, prior to being dipped in a solution to form the tissue stimulator of FIG. 12.

As an example, an insulation material may be formed by dissolving polyurethane in a solvent to form a liquid solution. Referring to FIG. 13, an assembly 432 that includes the circuit board 102 equipped with the circuit components 104, the antenna 106, and the electrodes 108 may be dipped into the liquid solution to coat the assembly 432 with the liquid solution. Iterative dips may be performed to achieve a desired cylindrical shape and diameter of the tissue stimulator 400. For example, dip coating applies the liquid solution layer by layer. After an initial dip, the assembly is air dried for a period of time to evaporate a liquefying chemical component of the liquid solution, and then the process is repeated to iteratively increase a diameter of the assembly. The coating may be subsequently removed from at least a portion or all of each electrode 108.

Figure 14:
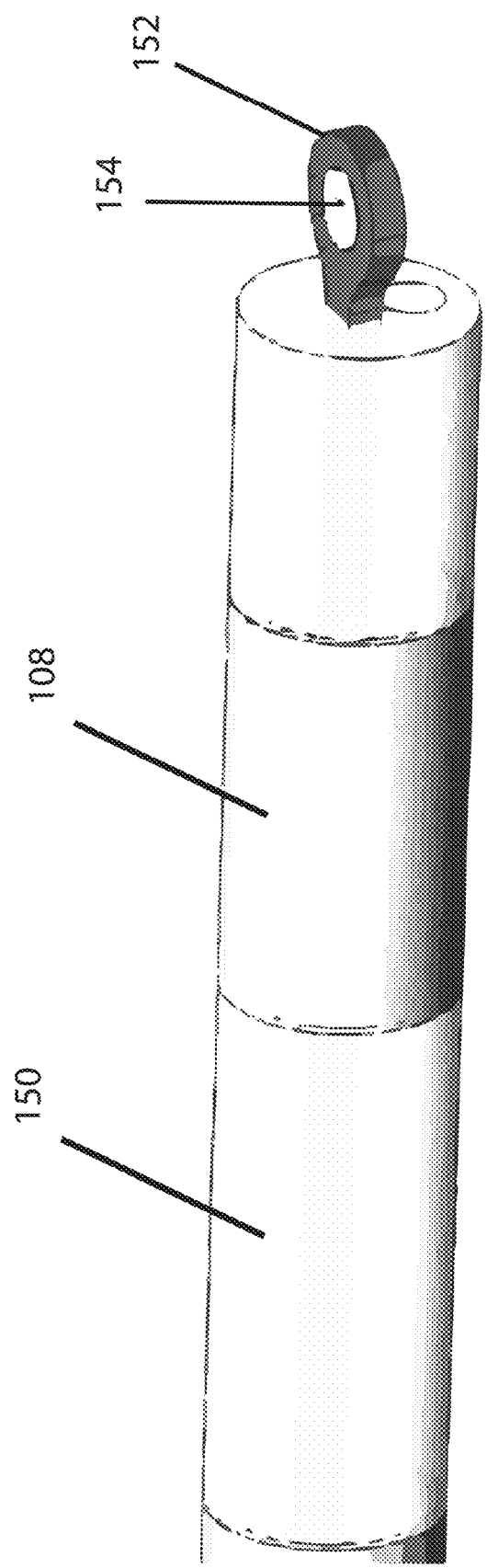
FIG. 14 an enlarged perspective view of an end of a circuit board of one or more of the tissue stimulators of FIG. 1, 11, or 12.
Figure 15:
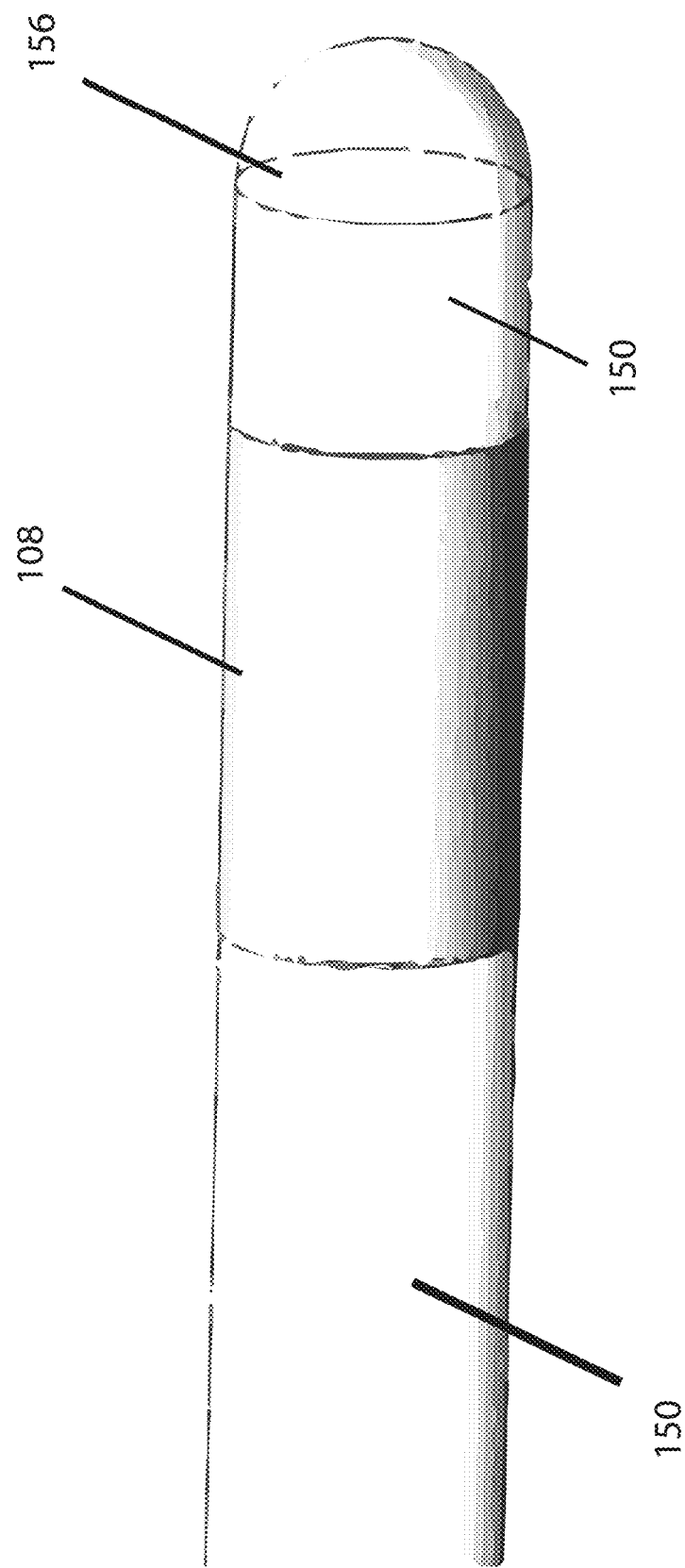
FIG. 15 is an enlarged perspective view of an end the tissue stimulators of one or more of FIG. 1, 11, or 12 with an end cap.

Referring to FIG. 14, either or both ends 152 of the circuit board 102 may be formed with a circular opening 154 that may be used for securing the circuit board 102 to a fixture during any of the above-discussed manufacturing processes. Referring to FIG. 15, in some embodiments, either or both ends 152 of the circuit board 102 may be clipped off and replaced with smooth, hemispherical caps 156 on the tissue stimulator 100, 300, 400 (e.g., via adding hemispherical caps 156 by subsequently dipping the tissue stimulator 100, 300, 400 into an insulating material, or injection molding additional insulating material, or gluing an existing hemispherical cap 156 to the tissue stimulator 100, 300, 400).

Figure 16:
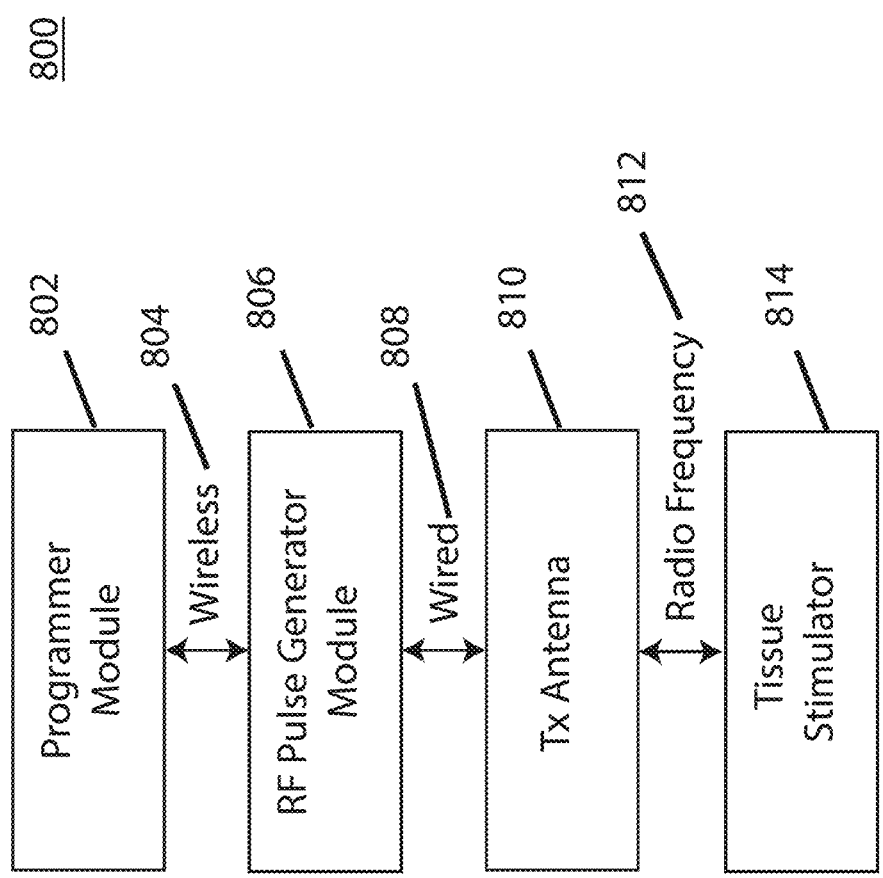
FIG. 16 is a system block diagram of a neural stimulation system configured to use the tissue stimulator of FIG. 1.

Referring to FIG. 16, any of the tissue stimulators 100, 300, 400 may be embodied as a tissue stimulator 814 of a neural stimulation system 800. The neural stimulation system further includes a radio frequency (RF) pulse generator module 806 that is located exterior to the patient (e.g., handheld by the patient or clinical technician), a transmit (TX) antenna 810 that is connected to the RF pulse generator 806 and positioned against a skin surface of the patient, and a programmer module 802 that runs a software application. The neural stimulation system 800 is configured to send electrical pulses to a nearby (e.g., adjacent or surrounding) target nerve tissue to stimulate the target nerve tissue by using remote radio frequency (RF) energy, without cables and without inductive coupling, to power the tissue stimulator 814. Accordingly, the tissue stimulator 814 is provided as a passive tissue stimulator in the neural stimulation system 800. In some examples, the target nerve tissue is in the spinal column and may include one or more of the spinothalamic tracts, the dorsal horn, the dorsal root ganglia, the dorsal roots, the dorsal column fibers, and the peripheral nerves bundles leaving the dorsal column or the brainstem. In some examples, the target nerve tissue may include one or more of cranial nerves, abdominal nerves, thoracic nerves, trigeminal ganglia nerves, nerve bundles of the cerebral cortex, deep brain, sensory nerves, and motor nerves.

In some embodiments, the software application supports a wireless connection 804 (e.g., via Bluetooth®). The software application may enable the user to view a system status and system diagnostics, change various parameters, increase and decrease a desired stimulus amplitude of the electrical pulses, and adjust a feedback sensitivity of the RF pulse generator module 806, among other functions.

The RF pulse generator module 806 includes stimulation circuitry, a battery to power generator electronics, and communication electronics that support the wireless connection 804. In some embodiments, the RF pulse generator module 806 is configured to be worn external to the body, and the TX antenna 810 (e.g., located external to the body) is connected to the RF pulse generator module 806 by a wired connection 808. Accordingly, the RF pulse generator module 806 and the TX antenna 810 may be incorporated into a wearable accessory (e.g., a belt or a harness design) or a clothing article such that electric radiative coupling may occur through the skin and underlying tissue to transfer power and/or control parameters to the tissue stimulator 814.

The TX antenna 810 may be coupled directly to tissues within the body to create an electric field that powers the implanted tissue stimulator 814. The TX antenna 810 communicates with the tissue stimulator 814 through an RF interface. For instance, the TX antenna 810 radiates an RF transmission signal that is modulated and encoded by the RF pulse generator module 806. The tissue stimulator 814 includes one or more antennas (e.g., dipole antennas) that may receive and transmit through an RF interface 812. In particular, the coupling mechanism between the TX antenna 810 and the one or more antennas on the tissue stimulator 814 is electrical radiative coupling and not inductive coupling. In other words, the coupling is through an electric field rather than through a magnetic field. Through this electrical radiative coupling, the TX antenna 810 may provide an input signal to the tissue stimulator 814.

In addition to the one or more antennas, the tissue stimulator 814 further includes internal receiver circuit components that may capture the energy carried by the input signal sent from the TX antenna 810 and demodulate the input signal to convert the energy to an electrical waveform. The receiver circuit components may further modify the waveform to create electrical pulses suitable for stimulating the target neural tissue. The tissue stimulator 814 further includes electrodes that may deliver the electrical pulses to the target neural tissue. For example, the circuit components may include wave conditioning circuitry that rectifies the received RF signal (e.g., using a diode rectifier), transforms the RF energy to a low frequency signal suitable for the stimulation of neural tissue, and presents the resulting waveform to an array of the electrodes. In some implementations, the power level of the input signal directly determines an amplitude (e.g., a power, a current, and/or a voltage) of the electrical pulses applied to the target neural tissue by the electrodes. For example, the input signal may include information encoding stimulus waveforms to be applied at the electrodes.

In some implementations, the RF pulse generator module 806 may remotely control stimulus parameters of the electrical pulses applied to the target neural tissue by the electrodes and monitor feedback from the tissue stimulator 814 based on RF signals received from the tissue stimulator 814. For example, a feedback detection algorithm implemented by the RF pulse generator module 806 may monitor data sent wirelessly from the tissue stimulator 814, including information about the energy that the tissue stimulator 814 is receiving from the RF pulse generator module 806 and information about the stimulus waveform being delivered to the electrodes. Accordingly, the circuit components internal to the tissue stimulator 814 may also include circuitry for communicating information back to the RF pulse generator module 806 to facilitate the feedback control mechanism. For example, the tissue stimulator 814 may send to the RF pulse generator module 806 a stimulus feedback signal that is indicative of parameters of the electrical pulses, and the RF pulse generator module 806 may employ the stimulus feedback signal to adjust parameters of the signal sent to the tissue stimulator 814.

In order to provide an effective therapy for a given medical condition, the neural stimulation system 800 may be tuned to provide the optimal amount of excitation or inhibition to the nerve fibers by electrical stimulation. A closed loop feedback control method may be used in which the output signals from the tissue stimulator 814 are monitored and used to determine the appropriate level of neural stimulation current for maintaining effective neuronal activation.

Alternatively, in some cases, the patient may manually adjust the output signals in an open loop control method.

Figure 17:
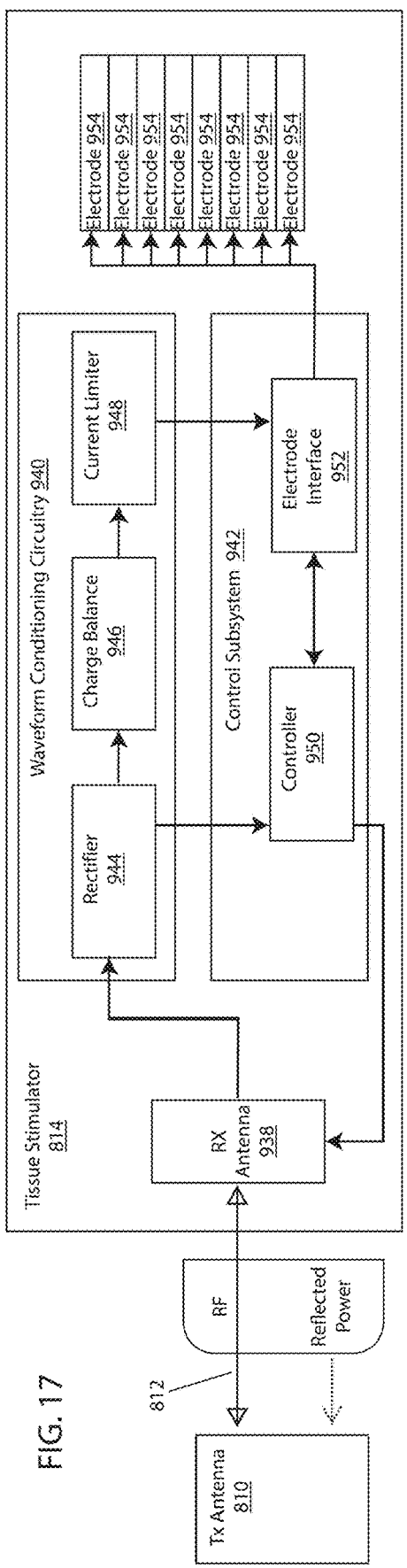
FIG. 17 is a block diagram of the neural stimulation system of FIG. 16 interacting with a tissue stimulator.

FIG. 17 shows a detailed diagram of the neural stimulation system 800. Instructions from the programmer module 802 of FIG. 16 allows a user to input or adjust instruction sets in order to adjust various parameter settings (e.g., in some cases, in an open loop fashion). The instruction sets (e.g., and other information) may be sent via the wireless connection 804 (e.g., via a Bluetooth or Wi-Fi connection) to the RF pulse generator module 806. Alternatively, a wired connection may be used. The RF pulse generator module 806 may include a power supply subsystem that provides power to the components of the RF pulse generator module 806.

The programmer module 802 may be utilized by multiple types of users (e.g., patients and others), such that the programmer module 802 may serve as a patient's control unit or a clinician's programmer unit. The programmer module 802 may be used to send stimulation parameters to the RF pulse generator module 806. The stimulation parameters that may be controlled may include a pulse amplitude in a range of 0 mA to 20 mA, a pulse frequency in a range of 0 Hz to 2000 Hz, and a pulse width in a range of 0 ms to 2 ms. In this context, the term pulse refers to the phase of the waveform that directly produces stimulation of the tissue. Parameters of a charge-balancing phase (described below) of the waveform may similarly be controlled. The user may also optionally control an overall duration and a pattern of a treatment.

The tissue stimulator 814 or the RF pulse generator module 806 may be initially programmed to meet specific parameter settings for each individual patient during an initial implantation procedure. Because medical conditions or the body itself may change over time, the ability to readjust the parameter settings may be beneficial to ensure ongoing efficacy of the neural modulation therapy.

Signals sent by the RF pulse generator module 806 to the tissue stimulator 814 may include both power and parameter attributes related to the stimulus waveform, amplitude, pulse width, and frequency. The RF pulse generator module 806 may also function as a wireless receiving unit that receives feedback signals from the tissue stimulator 814. To that end, the RF pulse generator module 806 includes microelectronics or other circuitry to handle the generation of the signals transmitted to the tissue stimulator 814, as well as feedback signals received from tissue stimulator 814.

Various parameter settings may be adjust the electrical pulses that will be applied to tissues via the electrodes. For instance, the parameter settings may affect one or more of the power, current level, voltage level, and/or shape of the electrical pulses. The programming of the stimulation parameters may be performed using the programming module 802 as described above to set a repetition rate, pulse width, amplitude, and waveform that will be transmitted by RF energy to a receive (RX) antenna 938 (e.g., or multiple RX antennas 938) within the tissue stimulator 814. The RX antenna 938 may be a dipole antenna or another type of antenna. A clinician user may have the option of locking and/or hiding certain settings within a programmer interface to limit an ability of a patient user to view or adjust certain parameters since adjustment of certain parameters may require detailed medical knowledge of neurophysiology, neuroanatomy, protocols for neural modulation, and safety limits of electrical stimulation.

The RF signal 812 may be sent to the TX antenna 810 to reach the RX antenna 938 through a depth of tissue.

In some implementations, the RF signal sent by the TX antenna 810 may simply be a power transmission signal used by tissue stimulator 814 to generate electric pulses. In other implementations, the RF signal sent by the TX antenna 810 may be a telemetry signal that provides instructions about various operations of the tissue stimulator 814. The telemetry signal may be sent by the modulation of the carrier signal through the skin. The telemetry signal is used to modulate the carrier signal (e.g., a high frequency signal) that is coupled to the antenna 938 and does not interfere with the input received on the same lead to power the tissue stimulator 814. In some embodiments, the telemetry signal and the powering signal are combined into one signal, where the RF telemetry signal is used to modulate the RF powering signal such that the tissue stimulator 814 is powered directly by the received telemetry signal. Separate subsystems in the tissue stimulator 814 harness the power contained in the signal and interpret the data content of the signal.

The sequence of remotely programmable RF signals received by the RX antenna 938 may be conditioned into waveforms that are controlled within the tissue stimulator 814 by the controller 950 and routed to the appropriate electrodes 954 that are located in proximity to the target nerve tissue. For instance, the RF signal transmitted from the RF pulse generator module 806 may be received by RX antenna 938 and processed by circuitry, such as waveform conditioning circuitry 940, within the tissue stimulator 814 to be converted into electrical pulses applied to the electrodes 954 through an electrode interface 952. In some implementations, the tissue stimulator 814 includes between two to sixteen electrodes 954.

The waveform conditioning circuitry 940 may include a rectifier 944, which rectifies the signal received by the RX antenna 938. The rectified signal may be fed to the controller 950 for receiving encoded instructions from the RF pulse generator module 806. The rectifier signal may also be fed to a charge balance component 946 that is configured to create one or more electrical pulses such that the one or more electrical pulses result in a substantially zero net charge at the one or more electrodes 954 (that is, the pulses are charge balanced). The charge balanced pulses are passed through the current limiter 948 to the electrode interface 952, which applies the pulses to the electrodes 954 as appropriate.

The current limiter 948 insures the current level of the pulses applied to the electrodes 954 is not above a threshold current level. In some implementations, an amplitude (for example, a current level, a voltage level, or a power level) of the received RF pulse directly determines the amplitude of the stimulus. In this case, it may be particularly beneficial to include current limiter 948 to prevent excessive current or charge being delivered through the electrodes 954, although the current limiter 948 may be used in other implementations where this is not the case. Generally, for a given electrode 954 having several square millimeters of surface area, it is the charge per phase that should be limited for safety (where the charge delivered by a stimulus phase is the integral of the current). But, in some cases, the limit may instead be placed on the current, where the maximum current multiplied by the maximum possible pulse duration is less than or equal to the maximum safe charge. More generally, the current limiter 948 acts as a charge limiter that limits a characteristic (for example, a current or duration) of the electrical pulses so that the charge per phase remains below a threshold level (typically, a safe-charge limit).

In the event the tissue stimulator 814 receives a "strong" pulse of RF power sufficient to generate a stimulus that would exceed the predetermined safe-charge limit, the current limiter 948 may automatically limit or "clip" the stimulus phase to maintain the total charge of the phase within the safety limit. The current limiter 948 may be a passive current limiting component that cuts the signal to the electrodes 954 once the safe current limit (the threshold current level) is reached. Alternatively, or additionally, the current limiter 948 may communicate with the electrode interface 952 to turn off all electrodes 954 to prevent tissue damaging current levels.

A clipping event may trigger a current limiter feedback control mode. The action of clipping may cause the controller to send a threshold power data signal to the RF pulse generator module 806. The feedback subsystem 912 detects the threshold power signal and demodulates the signal into data that is communicated to the controller subsystem 914. The controller subsystem 914 algorithms may act on this current-limiting condition by specifically reducing the RF power generated by the RF pulse generator module 806, or cutting the power completely. In this way, the RF pulse generator module 806 may reduce the RF power delivered to the body if the tissue stimulator 814 reports that it is receiving excess RF power.

The controller 950 may communicate with the electrode interface 952 to control various aspects of the electrode setup and pulses applied to the electrodes 954. The electrode interface 952 may act as a multiplex and control the polarity and switching of each of the electrodes 954. For instance, in some implementations, the tissue stimulator 814 has multiple electrodes 954 in contact with the target neural tissue, and for a given stimulus, the RF pulse generator module 806 may arbitrarily assign one or more electrodes to act as a stimulating electrode, to act as a return electrode, or to be inactive by communication of assignment sent wirelessly with the parameter instructions, which the controller 950 uses to set electrode interface 952 as appropriate. It may be physiologically advantageous to assign, for example, one or two electrodes 954 as stimulating electrodes and to assign all remaining electrodes 954 as return electrodes.

Also, in some implementations, for a given stimulus pulse, the controller 950 may control the electrode interface 952 to divide the current arbitrarily (or according to instructions from the RF pulse generator module 806) among the designated stimulating electrodes. This control over electrode assignment and current control may be advantageous because in practice the electrodes 954 may be spatially distributed along various neural structures, and through strategic selection of the stimulating electrode location and the proportion of current specified for each location, the aggregate current distribution on the target neural tissue may be modified to selectively activate specific neural targets. This strategy of current steering may improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes. Furthermore, the frequency of repetition of this stimulus cycle may be synchronous for all of the electrodes 954. However, the controller 950, on its own or in response to instructions from the RF pulse generator module 806, may control electrode interface 952 to designate one or more subsets of electrodes to deliver stimulus waveforms with non-synchronous start and stop times, and the frequency of repetition of each stimulus cycle may be arbitrarily and independently specified.

For example, a tissue stimulator 814 having eight electrodes 954 may be configured to have a subset of five electrodes, called set A, and a subset of three electrodes, called set B. Set A may be configured to use two of its electrodes as stimulating electrodes, with the remainder being return electrodes. Set B may be configured to have just one stimulating electrode. The controller 950 could then specify that set A deliver a stimulus phase with 3 mA current for a duration of 200 us, followed by a 400 us charge-balancing phase. This stimulus cycle could be specified to repeat at a rate of 60 cycles per second. Then, for set B, the controller 950 could specify a stimulus phase with 1 mA current for duration of 500 us, followed by a 800 us charge-balancing phase. The repetition rate for the set B stimulus cycle may be set independently of set A (e.g., at 25 cycles per second). Or, if the controller 950 was configured to match the repetition rate for set B to that of set A, for such a case the controller 950 may specify the relative start times of the stimulus cycles to be coincident in time or to be arbitrarily offset from one another by some delay interval.

The control subsystem 942 of the tissue stimulator 814 may transmit informational signals, such as a telemetry signal, through the RX antenna 938 to communicate with the RF pulse generator module 806 during its receive cycle.

In some implementations, the controller 950 may arbitrarily shape the stimulus waveform amplitude, and may do so in response to instructions from the RF pulse generator module 806. The stimulus phase may be delivered by a constant-current source or a constant-voltage source, and this type of control may generate characteristic waveforms that are static. For example, a constant current source generates a characteristic rectangular pulse in which the current waveform has a very steep rise, a constant amplitude for the duration of the stimulus, and then a very steep return to baseline. Alternatively, or additionally, the controller 950 may increase or decrease the level of current at any time during the stimulus phase and/or during the charge-balancing phase. Thus, in some implementations, the controller 950 may deliver arbitrarily shaped stimulus waveforms such as a triangular pulse, sinusoidal pulse, or Gaussian pulse for example. Similarly, the charge-balancing phase may be arbitrarily amplitude-shaped, and similarly a leading anodic pulse (prior to the stimulus phase) may also be amplitude-shaped.

As described above, the tissue stimulator 814 may include a charge balance component 946. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units uC/cm2. In order to avoid the irreversible electrochemical reactions such as pH change, electrode dissolution as well as tissue destruction, no net charge should appear at the electrode-electrolyte interface, and it is generally acceptable to have a charge density less than 30 uC/cm2. Biphasic stimulating current pulses ensure that no net charge appears at the electrode 954 after each stimulation cycle and that the electrochemical processes are balanced to prevent net dc currents. The tissue stimulator 814 may be configured to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or negative-current, called the cathodic phase of the waveform. Stimulating electrodes may have both cathodic and anodic phases at different times during the stimulus cycle. An electrode 954 that delivers a negative current with sufficient amplitude to stimulate adjacent neural tissue is called a "stimulating electrode." During the stimulus phase, the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 946 uses one or more blocking capacitors placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitors may be used for each electrode, or a centralized capacitors may be used within the stimulator circuitry prior to the point of electrode selection. The RC network may block direct current (DC). However, the RC network may also prevent low-frequency alternating current (AC) from passing to the tissue. The frequency below which the series RC network essentially blocks signals is commonly referred to as the cutoff frequency, and in some embodiments, the design of the stimulator system may ensure that the cutoff frequency is not above the fundamental frequency of the stimulus waveform. In the example neural stimulation system 800, the tissue stimulator 814 may have a charge-balance capacitor with a value chosen according to the measured series resistance of the electrodes and the tissue environment in which the stimulator is implanted. By selecting a specific capacitance value, the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be configured to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the tissue stimulator 814 may create a drive-waveform envelope that follows the envelope of the RF pulse received by the RX antenna 938. In this case, the RF pulse generator module 806 may directly control the envelope of the drive waveform within the tissue stimulator 814, and thus no energy storage may be required inside of the tissue stimulator 814, itself. In this implementation, the stimulator circuitry may modify the envelope of the drive waveform or may pass it directly to the charge-balance capacitor and/or electrode-selection stage.

In some implementations, the tissue stimulator 814 may deliver a single-phase drive waveform to the charge balance capacitor or it may deliver multiphase drive waveforms. In the case of a single-phase drive waveform (e.g., a negative-going rectangular pulse), this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the tissue stimulator 814 facilitates the discharge of the charge-balance capacitor. In some implementations, using a passive discharge phase, the capacitor may allow virtually complete discharge prior to the onset of the subsequent stimulus pulse.

In the case of multiphase drive waveforms, the tissue stimulator 814 may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, may have the advantage of reducing the amplitude of the stimulus phase required to excite tissue.

In some implementations, the amplitude and timing of stimulus and charge-balancing phases is controlled by the amplitude and timing of RF pulses from the RF pulse generator module 806, and in other implementations, this control may be administered internally by circuitry onboard the tissue stimulator 814, such as controller 950. In the case of onboard control, the amplitude and timing may be specified or modified by data commands delivered from the pulse generator module 806.

While the RF pulse generator module 806 and the TX antenna 810 have been described and shown as separate components, in some embodiments, the RF pulse generator module 806 and the TX antenna 810 may be physically located in the same housing or other packaging. Furthermore, while the RF pulse generator module 806 and the TX antenna 810 have been described and shown as located external to the body, in some embodiments, either or both of the RF pulse generator module 806 and the TX antenna 810 may be configured to be implanted subcutaneously. While the RF pulse generator module 806 and the TX antenna 810 have been described and shown as coupled via a wired connection 808, in some embodiments (e.g., where the RF pulse generator module 806 is either located externally or implanted subcutaneously), the RF pulse generator module 806 and the TX antenna 810 may be coupled via a wireless connection.

FIGS. 18A, 18B, and 18C show a circuit board and various molds that may be used with an injection molding process. FIG. 18A shows an example of circuit board 102 and two electrodes 108 before overmolding. FIG. 18B shows an example of two dies that together form a first mold with a cavity having round and half-round cross-sections. Specifically, FIG. 18B shows a first die 1801 and a second die 1802 that may be used together to create a mold for overmolding an insulating material over circuit board 102. For simplicity, the first die 1801 and the second die 1802 are shown next to each other but represent two separate dies (reflected in the broken line between them). The first die 1801 may include a first cavity 1803 that has a half-round cross-section, sized to accept a portion of electrodes 108. The length of cavity 1803 is sized to extend longitudinally past two or more electrodes. The die 1801 may include additional cavities 1804 to accept at least some of circuit board 102.

As die 1801 may be used with die 1802, each of dies 1801 and 1802 may include cavities (1804 and 1806) to accommodate circuit board 102 or only one of dies 1801 or 1802 may have a respective cavity while the other die lacks cavities, with the size of the cavity 1804 or 1806 sized in depth accordingly. The die 1801 may include one or more sprues 1807. The die 1802 may include two or more cavities 1805 to accept a complimentary portion of electrodes 108. The cavities 1805 may be fed via sprues 1808. In practice, both of sprues 1807 and 1808 may be used or only one of sprues 1807 and 1808 (or both used but having different sizes).

The cavities 1805 may be separated from each other to restrict the insulating material from overmolding the side of circuit board 102 facing (or recessed in) die 1802. Using the combination of the die 1801 and 1802, a first longitudinal portion of circuit board 1802 may be overmolded while a second longitudinal portion is supported by die 1802 at a fixed position along the longitudinal axis of the circuit board 102.

FIG. 18C shows an example of two dies that together form a mold with a cavity having a round cross section. The first die 1801 and a third die 1809 may be used together to create a mold for overmolding an insulating material over circuit board 102. For simplicity, the first die 1801 and the third die 1809 are shown next to each other but represent two separate dies (reflected in the broken line between them). For simplicity, a first die of FIG. 18C is identified using similar reference numerals to those of die 1801 of FIG. 18B. The first die 1801 may include a first cavity 1803 that has a half-round cross-section, sized to accept a portion of electrodes 108. The length of cavity 1803 is sized to extend longitudinally past two or more electrodes. The die 1801 may include additional cavities 1804 to accept at least some of circuit board 102. A third die 1809 may include complementary cavities to those of first die 1801. For example, the third die 1809 may include a half-round cavity 1810 and cavities 1811. The third die 1809 may further include sprues 1812, 1813, and/or 1814. The sprue 1812 is positioned to be used with sprue 1807. Sprue 1813 is shown in broken lines as it may not be needed if the corresponding sprue or sprues 1807 are sized to accommodate the inflow of insulating material. Further, sprue 1814, shown offset from any sprue in die 1801, may not be needed.

The mold of FIG. 18C may be used to overmold circuit board 102 in a single injection process, in which the insulating material surrounds all sides of circuit board 102. Additionally or alternative, the mold of FIG. 18C may be used as a second (or subsequent) mold in a double (or multiple) injection process. In a double injection process, a first die (e.g., that of FIG. 18B) is used to overmold a first portion of the circuit board. Next, a second die (e.g., that of FIG. 18C) may be used to overmold a second or remaining portion of the circuit board. Further, additional molds may be used to overmold yet additional portions not completed using the first two molds.

As an example of a double injection molding process, the first mold of FIG. 18B may be used to overmold a first portion of the circuit board 102. Next, the half-overmolded circuit board may be placed in the mold of FIG. 18C. If placed in the same orientation in die 1801 of FIG. 18B into die 1801 of FIG. 18C, the already overmolded portion of circuit board 102 may fill cavity 1803 of FIG. 18C. This orientation may prevent insulation material from flowing through sprues 1807 of FIG. 18C into cavity 1803 as cavity 1803 is already occupied by the electrodes and overmolded portion of circuit board 102. In this example, sprue 1814 may be used to flow the insulation material to the not-yet overmolded portion of circuit board 102 (i.e., the portion restricted from being overmolded by the minimal to lack of cavities between cavities 1805 of die 1802. Using this double molding process, the flexible circuit board 102 may be accurately positioned in the middle of the insulation material. In some instances, using only a single injection process may deflect the circuit board 102 to abut a side of the cavity 103, resulting in an edge of circuit board 102 not being fully encapsulated and creating a rough portion on the surface of the tissue stimulator.

The resulting second overmolding injection of insulating material may complete the overmolding process for the tissue stimulator. Additionally or alternative, subsequent overmolding processes may be used to further overmold the tissue stimulator or other portions of the tissue stimulator. Further, the overmolding injection may be a high pressure injection, a low pressure injection, or a gravity fed injection.

Figure 19A:
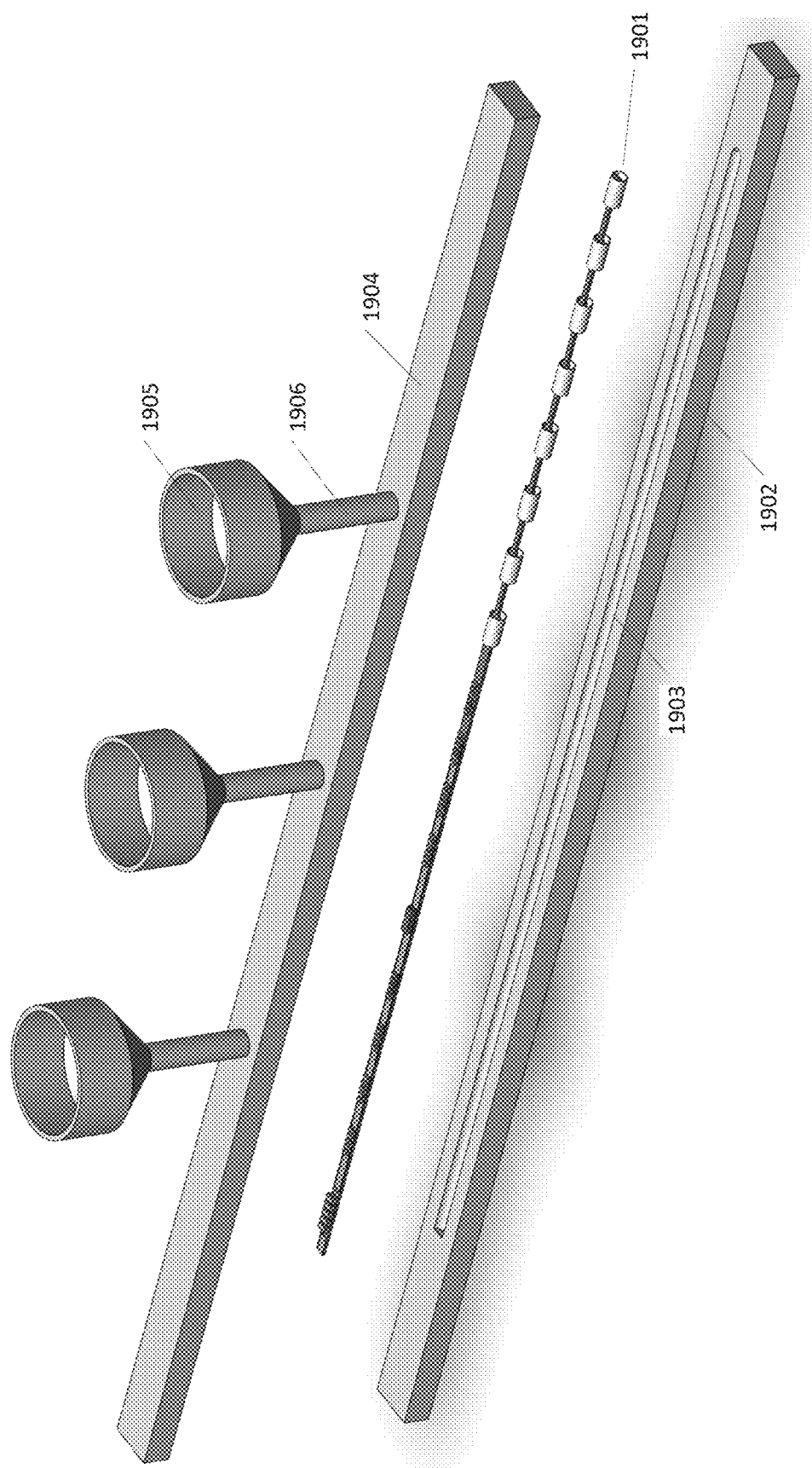
FIG. 19A shows a perspective view of overmolding using gravity to feed an insulation material into a mold.

FIG. 19A shows a perspective view of overmolding using gravity to feed an insulation material into a mold. A circuit board 1901 with electrodes and circuit components may be placed into a lower portion of cavity 1903 of a first die 1902. A second die 1904 with an upper portion of cavity 1903 (not shown) is connected to hoppers 1905 via nozzles 1906. In FIG. 19A, sprues (not shown) connect nozzles 1906 to the cavity 1903 formed between dies 1902 and 1904. Once closed, insulating material is permitted to flow from hoppers 1905, via gravity, to fill available spaces around the circuit board 1901.

FIG. 19B is a side view of the mold of FIG. 19A before overmolding of the insulating material. The circuit board 1901 rests in cavity 1903 between die 1902 and 1904. Hoppers 1905 are connected, via nozzles 1906, to cavity 1903. FIG. 19C is a side view of the mold of FIG. 19A with the insulating material 1907 filling cavity 1903. FIG. 19D shows an enlarged view of a resulting tissue stimulator 1908 removed from the mold of FIG. 19C. The tissue stimulator 1908 includes a portion 1909 of overmolding covering circuit components, a portion 1910 of overmolding covering other area of the circuit board 1901 including, for example, an antenna, a portion 1911 of overmolding covering markers 1912 (e.g., electrodes and/or connection joints that do not receive power), and a portion 1913 comprising exposed electrodes 1914 and spaces 1915 between the electrodes 1914 where the spaces 1915 are overmolded. Dashed line 1916 represents a possible location where a first circuit board is joined to a second circuit board by electrical wires or cables, possibly increasing the overall flexibility of the tissue stimulator.

Figure 20:
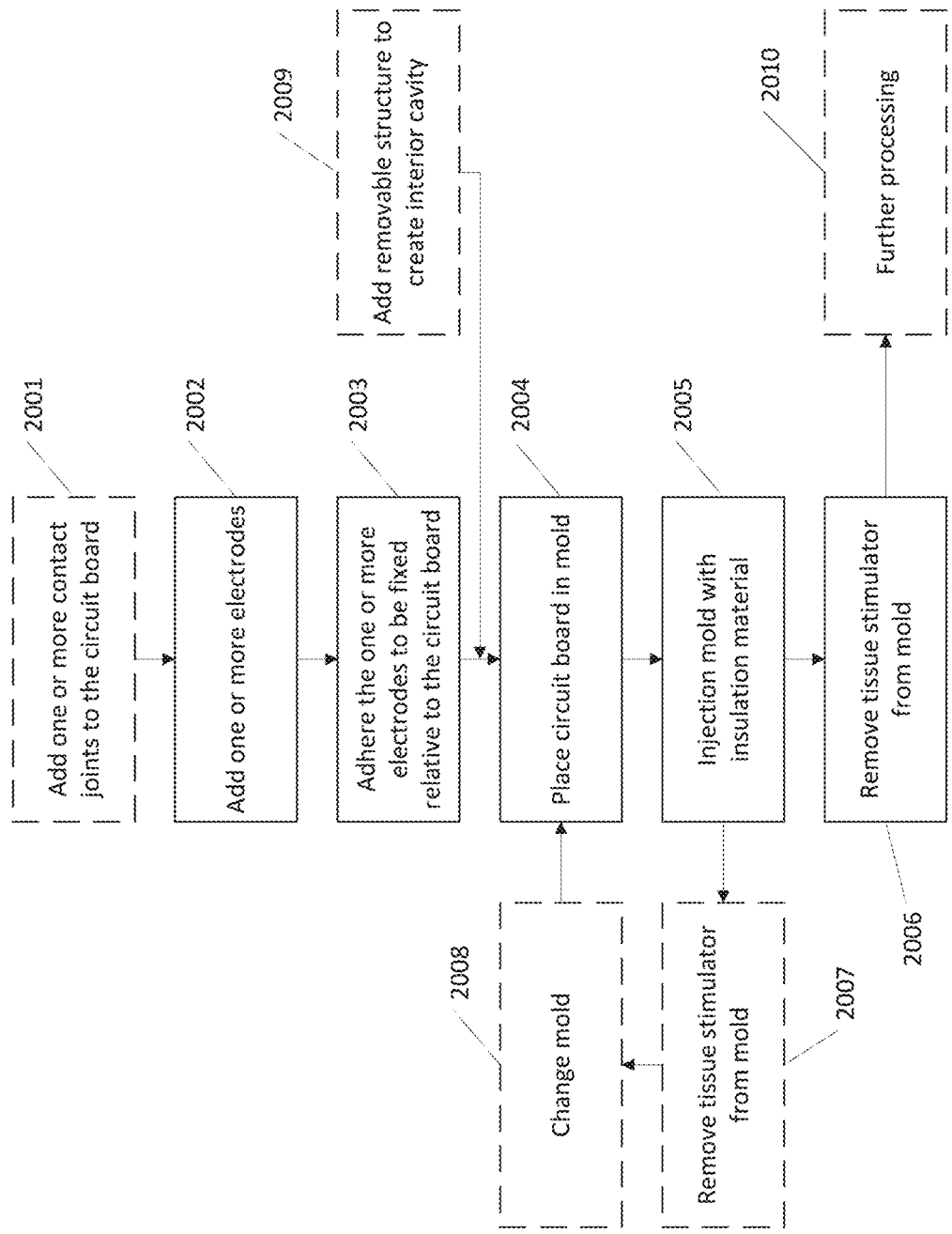
FIG. 20 is a flowchart showing an example manufacturing process using overmolding to add insulating material to a circuit board.

FIG. 20 is a flowchart showing an example manufacturing process using overmolding to add insulating material to a circuit board. In step 2002, one or more electrodes are added to a circuit board. In a processes where contact joints connect contact pads of a circuit board to electrodes, step 2002 may be preceded by step 2001 of adding one or more contact joints to the circuit board. Alternatively, if no contact joints are used, the electrodes may be added to directly contact the circuit board.

In step 2003, the electrodes are fixed in location relative to the circuit board (possible fixed to the contact joints or directed fixed to the contact board). In step 2009, a removable structure may be added to, for instance, a base of the circuit board and possibly within the electrodes such that, after molding, the removable structure may be removed to leave an interior cavity in the overmolded tissue stimulator.

In step 2004, the circuit board may be placed in a cavity within a mold. In step 2005, the mold may be injected (under high, low, or gravity-induced pressure) with the insulation material. In step 2006, the tissue stimulator may be removed from the mold. If additional processing is needed, it may be performed in step 2010.

If multiple injection molding processes are to be performed, after step 2005, the tissue stimulator may be removed in step 2007 from the mold (or at least from one of the dies of the mold) and the mold (or one of the dies) changed 2008. The process may continue with the placement of the circuit board in the new mold 2004.

Figure 21C:
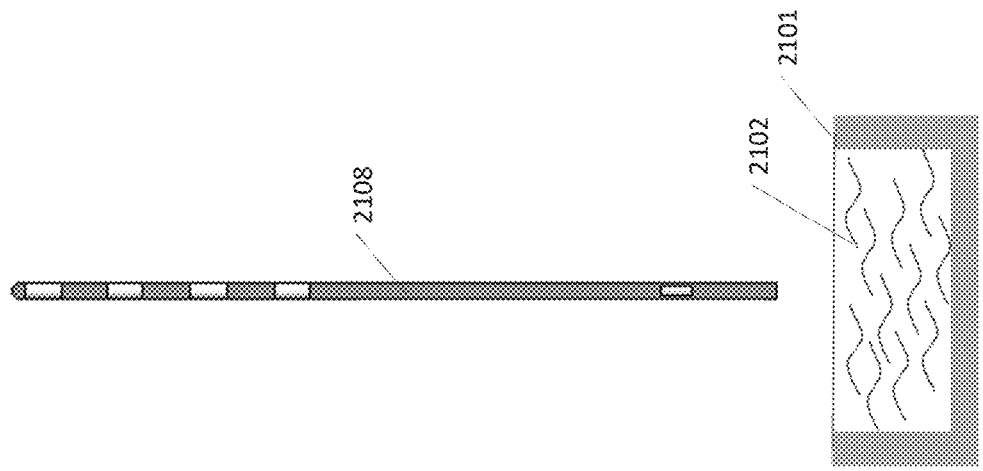
FIG. 21C shows a drying and cover removing portion of the insert molding process.
Figure 21B:
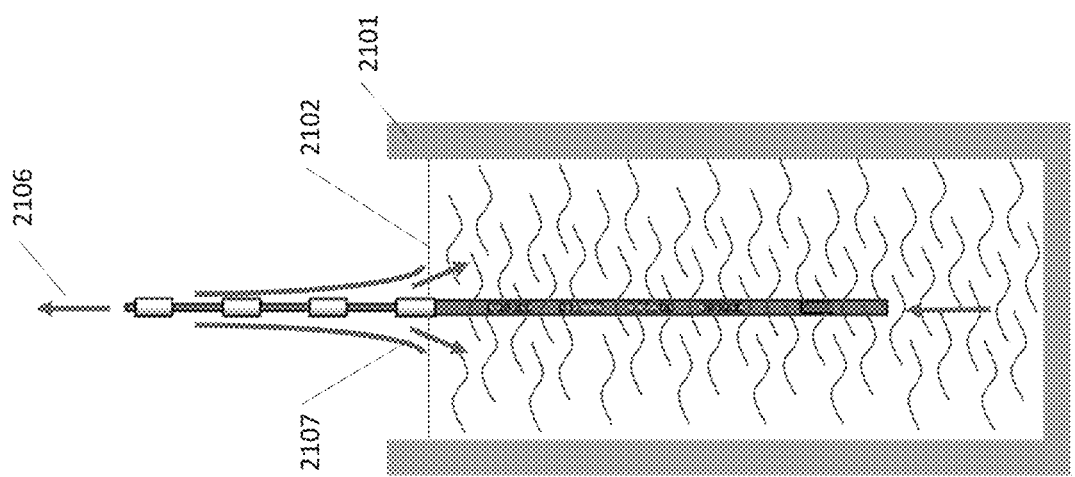
FIG. 21B shows a removal portion of the insert molding process.
Figure 21A:
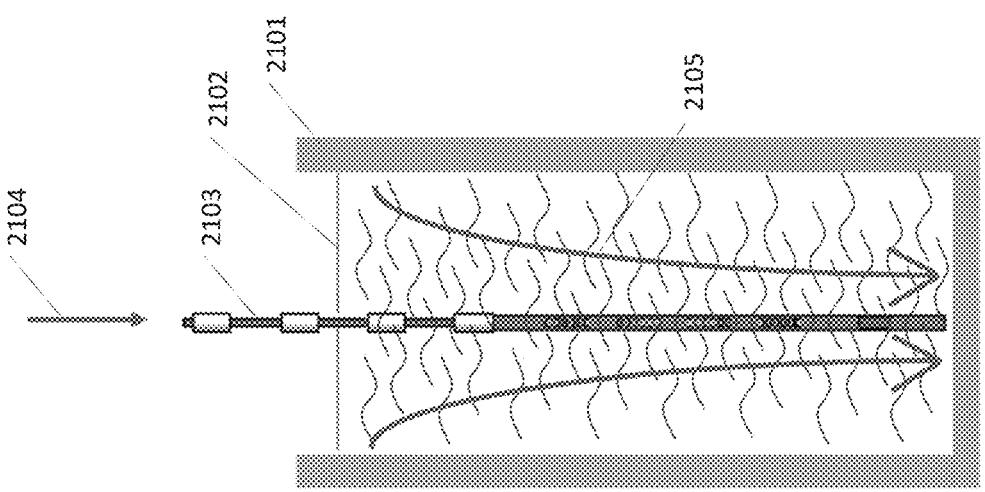
FIG. 21A shows a dipping portion of an insert molding process.

FIG. 21A shows a dipping portion of an insert molding process. A container 2101 contains a material in solution form (generally shown as liquid 2102). A circuit board 2103 is inserted in the direction of directional arrow 2104 into the liquid 2102. Either end may be inserted into the liquid. To prepare the electrodes for being dipped in FIG. 21A, the electrodes may be covered with a removal layer before dipping (e.g., tape, glue, or other removable barrier). Alternatively or additionally, the electrodes may be coated with a substance to which the liquid 2102 does not adhere.

FIG. 21B shows a removal portion of the insert molding process. The circuit board 2103 is removed from the liquid 2102 in the direction of arrow 2106. Excess liquid 2107 may flow back into container 2102.

FIG. 21C shows a drying and cover removing portion of the insert molding process. The circuit board 2103 may be allowed to at least partially dry before dipping again into liquid 2102. The circuit board 2103 may be repeatedly dipped and partially (or fully dried) to permit a solvent in the liquid adhering to the circuit board 2103 to evaporate, leaving the insulation material encapsulating portions of the circuit board 2103. The removable layer, if present, may be removed prior to or after the insulation material has cured. If the substance that reduced the ability of the liquid to adhere to the electrodes is present, it may be removed or permitted to remain on the surface of the electrodes.

Figure 22:
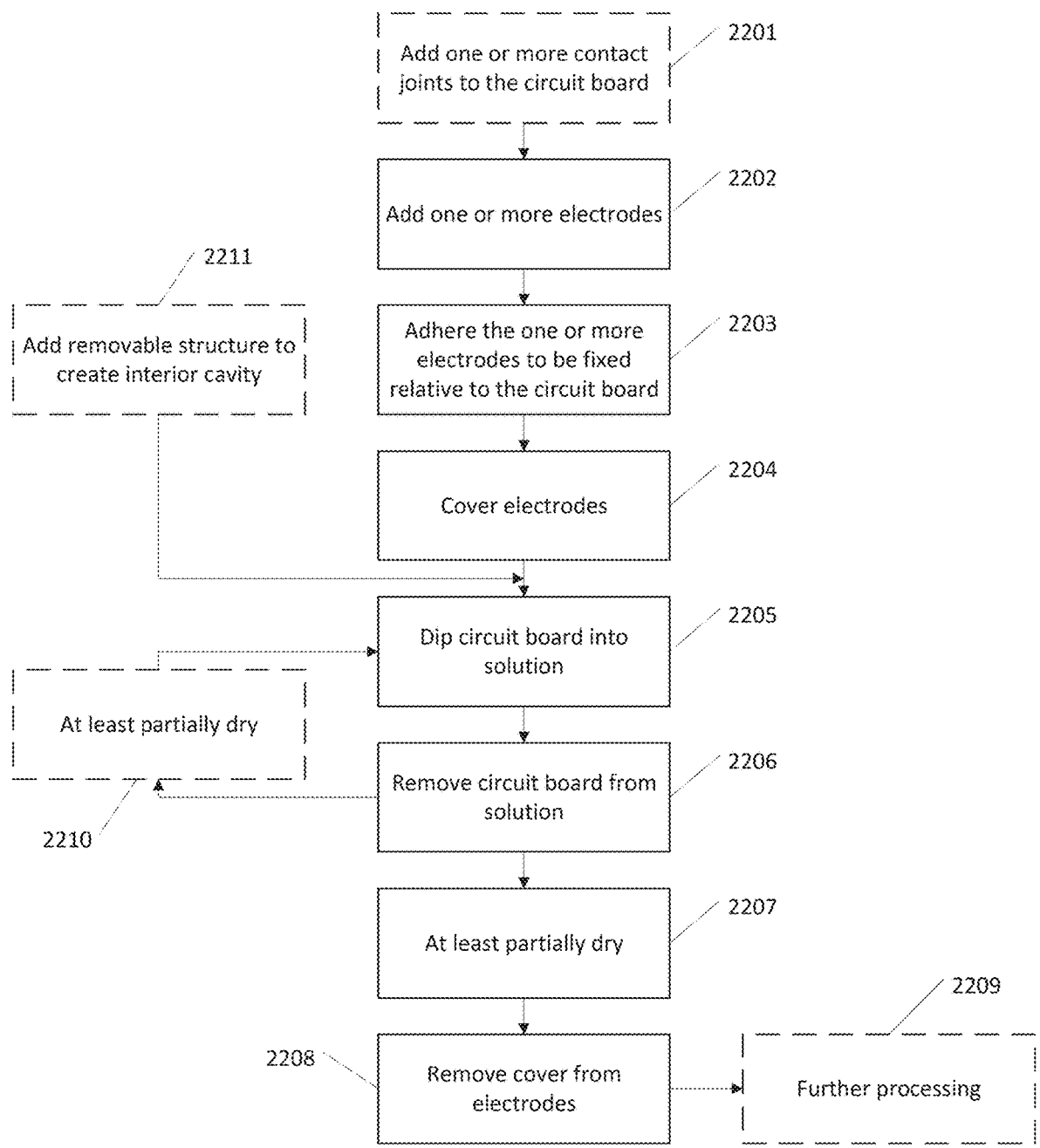
FIG. 22 is a flowchart showing an example manufacturing process using insert molding to add insulating material to a circuit board.

FIG. 22 is a flowchart showing an example process using insert molding to add insulating material to a circuit board. In step 2202, one or more electrodes are added to a circuit board. In a processes where contact joints connect contact pads of a circuit board to electrodes, step 2202 may be preceded by step 2201 of adding one or more contact joints to the circuit board. Alternatively, if no contact joints are used, the electrodes may be added to directly contact the circuit board.

In step 2203, the electrodes are fixed in location relative to the circuit board (possible fixed to the contact joints or directed fixed to the contact board). In step 2211, a removable structure may be added to, for instance, a base of the circuit board and possibly within the electrodes such that, after dipping, the removable structure may be removed to leave an interior cavity in the encapsulated tissue stimulator.

In step 2004, the electrodes may be covered with a removable layer (e.g., tape or glue) or coated to prevent adherence of the liquid to the electrodes. In step 2205, the circuit board may be dipped into the liquid. In step 2206, the circuit board may be removed from the liquid. In step 2207, the liquid is permitted to at least partially dry (and possibly fully dry) and in step 2208, the removable cover (if present on the electrodes) is removed. If additional processing is needed, it may be performed in step 2209.

If additional dips into the liquid are needed, in step 2210, the circuit board is permitted to a least partially dry and is dipped again in step 2205.

Figure 23:
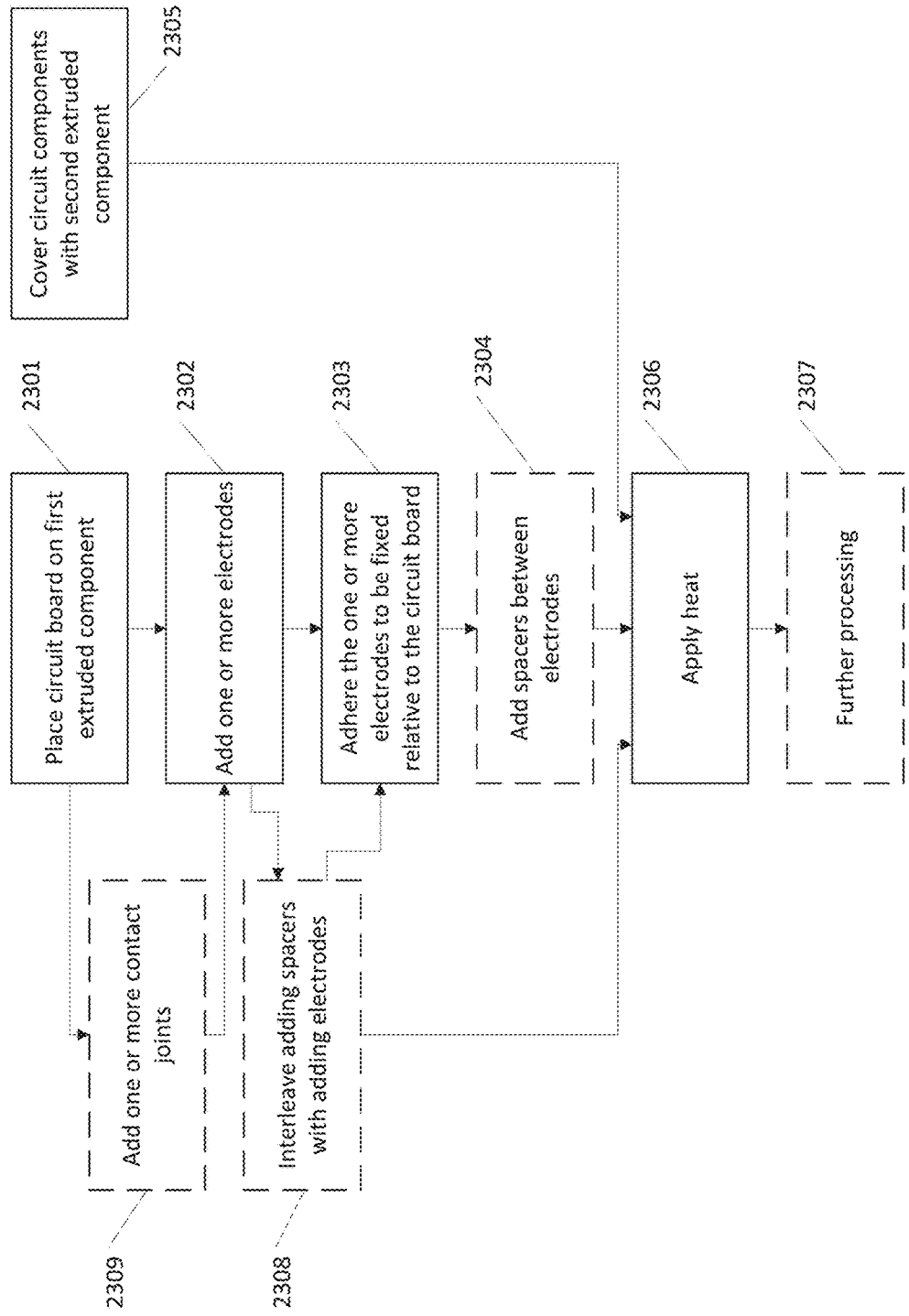
FIG. 23 is a flowchart showing an example manufacturing process using heat to reflow an insulating material over a circuit board.

FIG. 23 is a flowchart showing an example process using heat to reflow an insulating material over a circuit board. In step 2301, a circuit board is placed on a first extruded component. The first extruded component may include an inner channel. In step 2302, one or more electrodes may be added. If contact joints are to be included, they may be added in step 2309 before the electrodes are added. To position the electrodes relative to the circuit board, the electrodes may be threaded over the circuit board and first extruded component or clamped around them (or positioned using other approaches). In step 2303, the electrodes may be fixed in position relative to the circuit board. In step 2304, spacers may be added between the electrodes. In one example, as shown by dashed lines for step 2304, the spacers may be added after the electrodes have been fixed in location. Alternatively or additionally, and also shown in dashed lines, in step 2308, the spacers may be interleaved with electrodes as alternately positioned along the circuit board (e.g., by threading or clamping). In step 2305, the circuit components may be covered in step 2305 by second extruded component. While not shown, an additional heat-shrink material may optionally further cover portions of the assembly (e.g., a tube of heat-shrink material may cover the combination of the first extruded component, the circuit board, and the second extruded component).

In step 2306, heat may be applied. The applied heat may reflow the various heat-sensitive components to permit them to seal gaps on the periphery of the assembly, e.g., between electrodes and seams between the extruded components. If additional processing is needed, it may be performed in step 2307.

It will be recognized by the skilled person in the art, given the benefit of this disclosure, that the exact arrangement, sizes and positioning of the components in the figures is not necessarily to scale or required. Other embodiments of tissue stimulation systems, tissue stimulators, and methods of manufacturing such tissue stimulators are within the scope of the following claims.

What is claimed is:

1. A method of manufacturing a device, the method comprising:

adding one or more electrodes to a circuit board, the circuit board comprising an antenna and circuit components;

adhering the one or more electrodes to be fixed relative to the circuit board;

applying an insulation material to the circuit board such that the insulation material forms a housing that surrounds the circuit board, the circuit components, and the antenna, while preventing encapsulation of the one or more electrodes by the insulation material; and adding one or more contact joints at contact pad locations of the circuit board, wherein the adding one or more electrodes to a circuit board further comprises:

adding the electrodes after the contact joints have been added to the circuit board, wherein the applying the insulation material is a double injection process, wherein the applying the insulation material further comprises:

placing the circuit board with the one or more electrodes into a first mold;

flowing, into the first mold, the insulation material around at least the circuit board at locations relative to the antenna and the circuit components and between the electrodes, the first mold having at least one cavity having a first portion with a round cross-section and at least a second portion with a semi-round cross-section;

removing the circuit board with the one or more electrodes from the first mold;

changing the first mold to a second mold; and flowing the insulation material into the second mold, the second mold having at least one cavity having a round cross-section.

2. The method of manufacturing a device according to claim 1, further comprising:

forming an interior cavity from one end toward an opposite end.

3. The method of manufacturing a device according to claim 1, wherein the manufactured device has an average periphery, and wherein applying the insulation material further comprises:

forming, as part of applying the insulation material, structures extending away from the average periphery of the device.

4. The method of manufacturing a device according to claim 1, wherein the applying the insulation material comprises at least one of high pressure injection molding, low pressure injection molding, or gravity-fed injection molding.

* * * * *